(12) United States Patent
Chuang et al.

(10) Patent No.: US 10,087,273 B2
(45) Date of Patent: Oct. 2, 2018

(54) MULTIFUNCTIONAL POLYMERS

(71) Applicant: ISP Investments Inc., Wilmington, DE (US)

(72) Inventors: Jui-Chang Chuang, Wayne, NJ (US); Xuejun Liu, Whippany, NJ (US); Osama M. Musa, Kinnelon, NJ (US); Karen Winkowski, Springfield, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 127 days.

(21) Appl. No.: 14/384,111

(22) PCT Filed: Mar. 15, 2013

(86) PCT No.: PCT/US2013/032219
§ 371 (c)(1),
(2) Date: Sep. 9, 2014

(87) PCT Pub. No.: WO2013/162766
PCT Pub. Date: Oct. 31, 2013

(65) Prior Publication Data
US 2015/0044161 A1    Feb. 12, 2015

Related U.S. Application Data

(60) Provisional application No. 61/638,670, filed on Apr. 26, 2012.

(51) Int. Cl.
  *C08F 226/10*    (2006.01)
  *C08F 220/60*    (2006.01)
  *C08F 220/18*    (2006.01)
  *A01N 43/36*    (2006.01)

(52) U.S. Cl.
  CPC ............ *C08F 226/10* (2013.01); *A01N 43/36* (2013.01); *C08F 220/18* (2013.01); *C08F 220/60* (2013.01)

(58) Field of Classification Search
  CPC ................ C08F 226/10; C08F 220/60; C08F 2220/1858
  See application file for complete search history.

(56) References Cited

U.S. PATENT DOCUMENTS

| | | | | |
|---|---|---|---|---|
| 4,223,009 A * | 9/1980 | Chakrabarti | ........... | A61K 8/046 424/47 |
| 4,237,253 A * | 12/1980 | Jacquet | ................ | A61K 8/8152 424/47 |
| 4,923,694 A * | 5/1990 | Shih | ...................... | A61K 8/8182 424/70.15 |
| 5,045,617 A * | 9/1991 | Shih | ...................... | A61K 8/8182 524/548 |
| 5,219,906 A * | 6/1993 | Shih | ........................ | C08J 3/095 524/113 |
| 5,609,865 A * | 3/1997 | Liu | ...................... | A61K 8/8182 424/47 |
| 6,299,866 B1 * | 10/2001 | Liu | ...................... | A61K 8/8182 424/70.11 |
| 6,864,314 B1 * | 3/2005 | Yeung | ..................... | A61K 8/90 424/70.27 |
| 2003/0147929 A1 | 8/2003 | Kim et al. | | |
| 2008/0089853 A1 * | 4/2008 | Nguyen-Kim | ......... | A61K 8/817 424/61 |

OTHER PUBLICATIONS

Kuroda, Kenichi, and William F. DeGrado. "Amphiphilic polymethacrylate derivatives as antimicrobial agents." Journal of the American Chemical Society 127.12 (2005): 4128-4129.*
Dutta et al. "Nanostructure formation in aqueous solution of amphiphilic copolymers of 2-(N,N-dimethylaminoethyl) methacrylate and alkylacrylate: Characterization, antimicrobial activity, DNA binding, and cytotoxicity studies" International Journal of Pharmaceutics 414 (2011) pp. 298-311, entire document.
International Search Report, PCT/US2013/03032219 published on Oct. 31, 2013.

* cited by examiner

*Primary Examiner* — Bethany P Barham
*Assistant Examiner* — Peter Anthopolos
(74) *Attorney, Agent, or Firm* — Thompson Hine LLP; William J. Davis

(57) ABSTRACT

Described herein are multifunctional polymers comprising a first repeating unit having at least one pseudo-cationic moiety, a second repeating unit having at least a hydrophobic moiety, and a third repeating unit, where the weight-average molecular weight is less than about 10,000 Da. In one embodiment the polymers exhibit antimicrobial activity. Also provided are compositions formulated with the multifunctional polymers, and a method of providing antimicrobial activity.

18 Claims, No Drawings

MULTIFUNCTIONAL POLYMERS

BACKGROUND

Field of the Invention

The invention provides multifunctional polymers comprising a repeat unit having a pseudo-cationic moiety, a repeat unit having a hydrophobic moiety, and a third repeat unit. In one embodiment the polymer has a weight-average molecular weight of less than about 10,000 Da. In another embodiment the polymers exhibit antimicrobial activity. The polymers may be prepared by known polymerization methods, such as radical or condensation polymerization. Depending upon the repeating unit types and ratios, the resulting polymers can have a wide variety of physical and chemical properties. The multifunctional polymers of the invention can be employed in a wide variety of compositions. Also disclosed is a method of providing antimicrobial activity through the use of the multifunctional polymers.

Description of Related Art

Antimicrobial compounds are widely used in many formulations, where they may assist in killing or inhibiting the growth and presence of microbes as bacterium, fungus, or protozoan, or combinations thereof. In the personal care arts antimicrobial compounds may be called "preservatives," while in non-personal care applications—such as adhesives, coatings, inks, membranes, textiles, and paints—antimicrobial compounds may be called "biocides." Regardless, regulatory and environmental concerns have put limits on the selection and usage of traditional preservatives. Non-traditional antimicrobial compounds, such as multifunctional polymers, have attracted much attention in the chemical industry. Antimicrobial polymers are nonvolatile, do not penetrate the skin, have better long-term efficiency and possibly higher selectivity compared to traditional preservatives. Antimicrobial polymers also minimize environmental problems by minimizing residual toxicity.

Multifunctional polymers are described in the following disclosures, each of which is incorporated herein by reference. De Grado, et al., in *J. Am. Chem. Soc.*, 2005, 127, 4128, and U.S. Pat. Appl. No. 2006/0024264 disclose the synthesis and uses of amphiphilic polymethacrylate derivatives as antimicrobial agents. Kuroda, et al., in *Chem. Eur. J.*, 2009, 15, 1123, describes the role of hydrophobicity in the antimicrobial and hemolytic activities of polymethacrylate derivatives. Gellman, et al., in *Org. Lett.*, 2004, 4, 557, discloses the biocidal activity of polystyrene derivatives bearing cationic properties through reversible amine protonation. U.S. Pat. No. 6,214,885 describes the use of polymers containing β-hydroxyalkylvinylamine units as biocides. U.S. Pat. No. 5,208,016 discloses antimicrobial resin compositions containing ethylene copolymer from radical polymerization of ethylene and dialkylaminoalkylacrylamide co-repeating units.

Other references related to these polymers include the following patents and patent applications: EP 40,498; GB 686,381; 730,463; 870,398; 922,878; 1,286,966; 1,329,033; JP 53,090,397; 57,161,859; U.S. Pat. Nos. 3,449,250; 3,555,001; 4,048,422; 4,058,491; 4,734,446; 4,767,616; 5,229,458; 5,352,729; 5,408,022; 5,449,775; 5,492,988; 5,756,181; 6,025,501; 6,071,993; 6,075,107; 6,299,866; 6,646,082; 6,682,725; 6,737,049; 6,838,078; 6,951,598; 7,033,607; 7,041,281; 7,323,163; 7,326,262; 7,592,040; 7,955,594; US 2005/0152855; 2006/0024264; 2007/0082196; 2007/0161519; 2007/0238807; 2009/0029129; 2009/0312214; 2010/00029838; 2010/00298504; 2010/0130678; 2010/0137455; 2010/0174040; 2011/0060166, and WO 2010/0014655; 2010/031144 and PCT/US13/030115.

Accordingly, there is a need for multifunctional polymers to alter or improve the physicochemical properties of such polymers.

SUMMARY

The invention provides polymers that are polymerized from (A) a first repeating unit A comprising at least one pseudo-cationic moiety, (B) a second repeating unit B comprising at least one hydrophobic moiety, and (C) a third repeating unit C, and wherein the weight-average molecular weight of said polymer is less than about 10,000 Da. The polymer may be a terpolymer or comprise more than three repeating units. Additionally, the polymers may be synthesized via radical or condensation polymerization techniques.

In one embodiment, the polymers may exhibit antimicrobial activity.

Also provided are compositions having one or more of the multifunctional polymers, as well as a method of providing antimicrobial activity.

DETAILED DESCRIPTION

Described herein are polymers that are polymerized from at least three repeating unit types that are distinctly different from those known in the related art. In one embodiment, the polymers may exhibit antimicrobial properties, such as being microbiocidal and/or microbiostatic, which may lend their use in any number of formulations that may benefit from this effect. As a non-limiting aspect of this embodiment, the polymers may exhibit a broad spectrum of activity against many different types of microbes, including activity against *S. aureus*, *E. coli*, and *P. aeruginosa*. In another non-limiting aspect, the polymers may be formulated into compositions.

As used herein, the following terms have the meanings set out below.

The term "microbe" refers to any bacterium, fungus, protozoan, and any combination thereof.

The term "antimicrobial" refers to a substance that kills or inhibits the growth of microbes such as bacterium, fungus, or protozoan, or combinations thereof. Antimicrobials may kill microbes (microbiocidal) and/or prevent the growth of microbes (microbiostatic). The term "antimicrobial activity" refers to activity that kills and/or inhibits the growth of one or more microbes.

The term "functionalized" refers to replacing one or more hydrogens with one or more non-hydrogen groups, for e.g., alkyl, alkoxy, cycloalkyl, alkenyl, cycloalkenyl, alkynyl, and/or aryl groups. Alkyl, alkenyl and/or alkynyl groups include $C_1$-$C_{60}$, more particularly $C_1$-$C_{36}$, and most particularly $C_1$-$C_{18}$ groups. Cycloalkyl groups include cyclopentane, cyclohexane, cycloheptane, and the like. Alkoxy groups include methoxy, ethoxy, n-propoxy, isopropoxy, and the like. Aryl groups include benzenes, naphthalenes (2 rings), anthracenes (3 rings), and the like.

The term "anion" refers to an ion with more electrons than protons, giving it a net negative charge.

The term "cation" refers to an ion with fewer electrons than protons, giving it a net positive charge.

The term "halogenated" refers to chloro, bromo, iodo and fluoro. In one embodiment halogen may be bromo and/or chloro.

The term "branched and unbranched alkyl groups" refers to alkyl groups which may be straight chained or branched.

The alkyl group may have from 1 to about 18 carbon atoms, more particularly, from 1 to about 10 carbon atoms, and yet more particularly from 1 to about 6 carbon atoms. Branched groups include iso-propyl, tert-butyl, sec-butyl, and the like.

The term "hydrocarbyl" refers to straight-chain and/or branched-chain groups comprising carbon and hydrogen atoms with optional heteroatom(s). Particularly, the hydrocarbyl group includes $C_1$-$C_{60}$, more particularly $C_1$-$C_{36}$, and most particularly $C_1$-$C_{18}$ alkyl and alkenyl groups optionally having one or more hetero atoms. The hydrocarbyl group may be mono-, di- or polyvalent.

The term "heteroatom" refers to oxygen, nitrogen, sulfur, silicon, and/or phosphorous. The heteroatom may be present as a part of one or more functional groups on the hydrocarbyl chain and/or as a part of the hydrocarbyl chain itself. When the heteroatom is a nitrogen atom, the nitrogen atom may be present in the form of a quaternary amine.

The term "generic substituent(s)" refer(s) to substituent(s) such as $R_1$-$R_6$, and subscripts a, b, and c used and defined in the invention.

The term "amphiphilic" refers to a compound possessing both hydrophilic (water-loving, polar) and hydrophobic (lipophilic, fat-loving, non-polar) properties. Such compounds are also referred to as amphipathic.

The term "C1-C20 alkyl" refers to groups such as: methyl, ethyl, n-propyl, iso-propyl, n-butyl, iso-butyl, sec-butyl, tert-butyl, n-pentyl, sec-pentyl, tert-pentyl, n-hexyl, n-heptyl, n-octyl, 2-ethylhexyl, n-nonyl, iso-nonyl, 2-propylheptyl, n-decyl, n-dodecyl, n-tridecyl, iso-tri-decyl, n-tetradecyl, n-hexydecyl, n-octadecyl and eicosyl.

The term "C1-C20 alkylene" refers to groups such as: methylene, ethylene, n-propylene, iso-propylene, n-butylene, iso-butylene, sec-butylene, tert-butylene, n-pentylene, sec-pentylene, tert-pentylene, n-hexylene, n-heptylene, n-octylene, 2-ethylhexylene, n-nonylene, iso-nonylene, 2-propylheptylene, n-decylene, n-dodecylene, n-tridecylene, iso-tri-decylene, n-tetradecylene, n-hexydecylene, n-octadecylene and eicosylene.

The term "pseudo-cationic moiety" refers to moiety comprising one or more functionalized and unfunctionalized nitrogen or phosphorus.

The term "repeating unit" refers to a small molecule that chemically bonds during polymerization to one or more repeating units of the same or different kind to form a polymer.

The term "(meth)acrylate" refers to both methacrylate and acrylate. Similarly, the term "(meth)acrylamide" refers to both methacrylamide and acrylamide.

The term "polymer" refers to a large molecule (macromolecule) comprising repeating structural units polymerized from one or more repeating units connected by covalent chemical bonds.

The term "polymerization" refers to methods for chemically reacting repeating units to form polymer chains. The type of polymerization method may be selected from a wide variety of methods. Such methods include, but are not limited to, free radical polymerization, such as classical radical polymerization and controlled radical polymerization, Nitroxide Mediation Polymerization (NMP), Atom Transfer Radical Polymerization (ATRP), and Reversible Addition Fragmentation Chain-Transfer (RAFT). The term polymerization" also refers to condensation polymerization methods.

The term "homopolymer" refers to a polymer comprising essentially one type of repeating unit. Homopolymers include polymers polymerized from one repeating unit that may be modified during or after polymerization, for example, by grafting, hydrolyzing, or end-capping. Homopolymers may be associated with solvent adducts.

The term "non-homopolymer" refers to a polymer obtained by polymerization of two or more different kinds of repeating units. The definition includes essentially all polymers that are not homopolymers. Nonlimiting examples of non-homopolymers include copolymers, terpolymers, tetramers, and the like, wherein the non-homopolymer may be a random, block, or an alternating polymer.

The term "hydrophilic" refers to a molecular entity that tends to be polar and water-soluble or water-miscible. A hydrophilic molecule or portion of a molecule may be charge-polarized and/or capable of hydrogen bonding enabling it to dissolve in water.

The term "hydrophobic" refers to a molecular entity that tends to be non-polar and non-water-soluble.

The term "inert solvent" refers to a solvent that does not interfere chemically with the reaction.

The term "lower molecular weight alcohols" refers to alcohols having from one to four carbon atoms. Examples of lower molecular weight alcohols include: methanol, ethanol, 1-propanol, 2-propanol, allyl alcohol, propargyl alcohol, 2-aminoethanol, ethylene glycol, methyl propargyl alcohol, 1-butyn-4-ol, 2-butyn-1-ol, 2-buten-1-ol, 2-butanol, 2-methyl-2-propanol, and tert-butanol. In various embodiments of the invention, the lower molecular weight alcohol may be methanol, ethanol, 1-propanol, 2-propanol, or tert-butanol, or combinations thereof.

The term "quaternary ammonium cation", also known as "quat," refers to a positively charged polyatomic ion having the structure $NR'_4{}^+$, wherein each of the four R' independently can be an alkyl group or an aryl group. Unlike the ammonium ion ($NH_4{}^+$) and primary, secondary, and tertiary ammonium cations, the quaternary ammonium cations are permanently charged, independent of the pH value of their solution. Accordingly, quaternary ammonium cations are accompanied by an anion (negative charge) to balance the overall charge.

The term "each independently selected from the group consisting of" means that when a group appears more than once in a structure, that group may be independently selected each time it appears. For example, in the structure below:

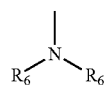

the generic substituent $R_6$ appears more than once. The term "each independently selected from the group consisting of" means that each generic substituent may be the same or different.

The term "weight-average molecular weight" refers to a method of describing the molecular weight of a polymer, and may be calculated by the equation:

$$M_w = \frac{\Sigma_i N_i M_i^2}{\Sigma_i N_i M_i}$$

wherein $N_i$ is the number of molecules having molecular weight $M_i$.

The term "number-average molecular weight" refers to another method of describing the molecular weight of a polymer, and may be calculated by the equation:

$$M_n = \frac{\Sigma_i N_i M_i}{\Sigma_i N_i}$$

wherein $N_i$ is the number of molecules having molecular weight $M_i$.

The term "personal care composition," also referred to as "cosmetics," refer to such illustrative non-limiting compositions as skin, sun, oil, hair, and preservative compositions, including those to alter the color, condition, or appearance of the skin. Potential personal care compositions include, but are not limited to, compositions for increased flexibility in styling, durable styling, increased humidity resistance for hair, skin, color cosmetics, water-proof/resistance, wear-resistance, and thermal protecting/enhancing compositions. Examples of personal care compositions include: skin lotion, skin crème, skin ointment, skin salve, anti-aging crème, moisturizer, deodorant, tanning agent, sun block, sunscreen, foundation, concealer, eyebrow pencil, eye shadow, eye liner, mascara, rouge, finishing powder, lipstick, lip gloss, nail polish, make-up remover, nail polish remover, shampoo, rinse-off conditioner, leave-on conditioner, hair styling gel, hair mousse, hair spray, styling aide, hair color, or hair color remover.

The term "performance chemicals composition" refers to any non-personal care composition. Performance chemicals compositions serve a broad spectrum of arts, and include non-limiting compositions such as: adhesives; agricultural, biocides, coatings, electronics, household-industrial-institutional (HI&I), inks, membranes, metal fluids, oilfield, paper, paints, plastics, printing, plasters, and wood-care compositions.

The term "oilfield formulation" refers to a composition that may be used in the exploration, extraction, recovery, or completion of any hydrocarbon-based fuel. Non-limiting examples of oilfield formulations include anti-agglomerants, emulsifiers, de-emulsifiers, gas hydrate inhibitors, kinetic hydrate inhibitors, shale swelling inhibitors, drilling fluids, drilling muds, friction reducers, rheology modifier, fracturing fluids, and/or scale inhibitors.

The term "coating formulation" refers to any composition suitable for application on a substrate in order to provide one or more desired functions, including, but not limited to protecting, smoothing, strengthening, decorating, color enhancing/altering, substrate preparing and/or texturizing. The substrate for a coating formulation may include, without limitation, paper, paper board, wood, inorganic substrate, woven and non-woven textiles, metal, leather, powder, plastic, polymer, glass, cement, ceramic, traffic, tile, rubber, sealant, cable, concrete, plasterboard, adhesives, fillers, primers, inks, fertilizers, pharmaceuticals, structural materials, molding, printing, inks, and the like. Examples of coating formulations include, without limitation, the following: paints, primers, stains, sealers, varnishes/polyurethanes, adhesives, waterproofers, wood hardeners. Coating formulations may be applied by brush, dauber, roll, strip/sheet, and/or trowel, or may be atomized and applied as a spray, mist, or droplet.

A "paint formulation" is a non-limiting, specific type of a "coating formulation". Paints may be water based or non-water based (i.e., solvent based). Paint formulations may be designed for any number of substrates, including wood, siding, dry wall, plaster, plastics, masonry, brick, tile, particle board, glass, stucco, concrete, and the like. Non-limiting examples of paints include exterior paints, interior paints, architectural paints, and automotive paints.

The term "imide" refers to an organic compound comprising two carbonyl groups (acyl groups) bound to a common nitrogen atom. The nitrogen atom in the imide functional group may or may not be substituted with an organic functional group.

The term "Jeffamine" is a brand name of The Huntsman Corporate and refers to polyetheramines containing primary amino groups attached to the end of a polyether backbone. The polyether may be based on either propylene oxide (PO), ethylene oxide (EO), or mixed PO/EO. The polyetheramines undergo typical amine reactions, often imparting increased flexibility, toughness, low viscosity, and low color. The wide range of molecular weight, amine functionality, repeating unit type, and distribution can provide flexibility in the design of new compounds or mixtures. Jeffamines are available from Huntsman Corporation, The Woodlands, Tex.

Multifunctional polymers have been discovered that are polymerized from at least repeating unit (or repeat unit) types: A first repeating unit A comprising at least one pseudo-cationic moiety, a second repeating unit B that comprises at least one hydrophobic moiety, and a third repeating unit C, and wherein the weight-average molecular weight of the polymer is less than about 10,000 Da. Without being bound by theory, it is believed that the combination of repeating units A and B contribute antimicrobial activity, and repeating unit C allows for additional performance functionality.

The polymers may be random, block, or alternating, or combinations thereof.

At least two broad categories of polymers are embraced by the invention, their repeating unit (or repeat unit) types determined in part by the polymerization method. Multifunctional polymers prepared by a radical polymerization approach are summarized first, followed by polymers synthesized by condensation polymerization. These polymers comprise at least one first repeating unit A, at least one second repeating unit B, and at least one third repeating unit C.

By a radical polymerization method, repeating unit A may be any repeating unit having at least one pseudo-cationic moiety. For example, repeating unit A may be an amino (meth)acrylate, amino (meth)acrylamide, or a repeating unit comprising a nitrogen or phosphorus heterocyclic ring, or combinations of these repeating units. These repeating units may exhibit pseudo-cationic behavior, e.g., in acid conditions, e.g., by protonation under acidic conditions.

In the embodiments wherein repeating unit A is an amino (meth)acrylate or an amino (meth)acrylamide, it may be represented by the structure:

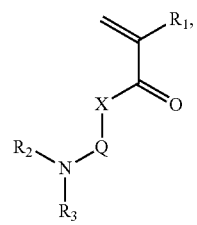

wherein
$R_1$, is selected from the group consisting of hydrogen, methyl, and combinations thereof;
$R_2$ and $R_3$ are independently selected from the group consisting of C1-C20 alkyl, Q is selected from the group consisting of functionalized and unfunctionalized alkylene, cycloalkylene, alkyleneoxy, alkenylene, and arylene; and X is O or NH or combinations thereof.

In the amino (meth)acrylate and amino (meth)acrylamide structure presented earlier, $R_1$ may be hydrogen or methyl, such that repeating unit A may be regarded as an amino (meth)acrylate or amino (meth)acrylamide:

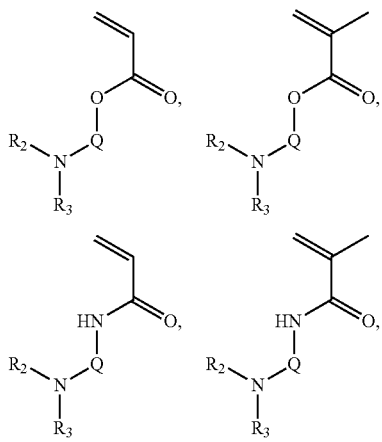

where $R_2$, $R_3$, and Q retain their earlier definitions. Particularly, Q may be C1-C8 alkylene, more particularly C2-C5 alkylene. $R_2$ and $R_3$ may be C1-C4 alkyl groups. Non-limiting examples of the second repeating unit include:

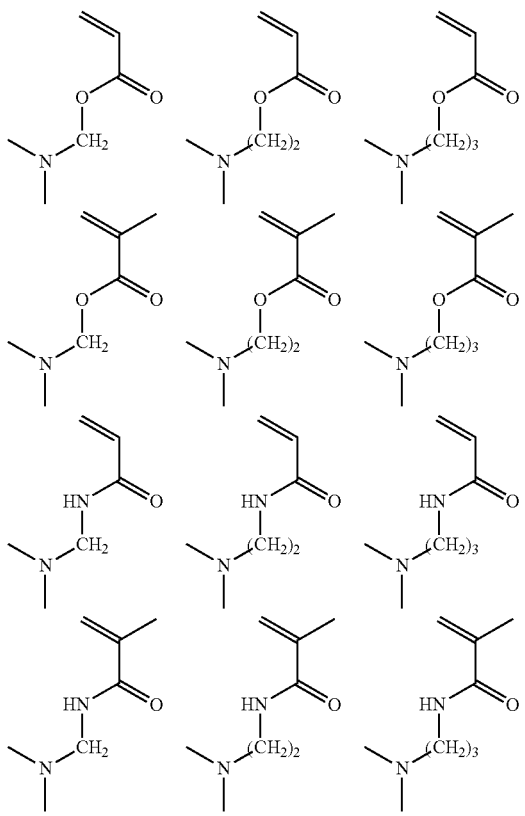

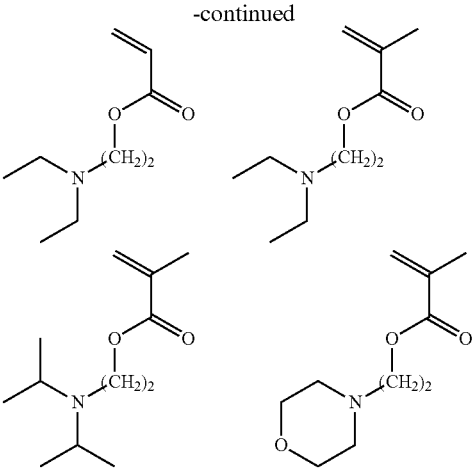

Optionally, repeating unit A may comprise a nitrogen or phosphorus heterocyclic ring, such as functionalized and unfunctionalized N-vinyl lactams, vinyl pyridines, vinyl imidazoles, and/or vinyl pyrazoles. Included in this aspect of the invention are the following polymerizable compounds: N-vinyl imidazole, N-vinyl benzimidazole, N-vinyl-pyrazole, N-vinyl-3-imidazoline, N—(C1-C20-alkyl)-N'-vinyl piperazine or 2-, 3- or 4-vinyl pyridine, and hydroxyethyl-imidazole (meth)acrylate. One or more C1-C20-alkyl groups, which can be substituents in the aforementioned repeating units can be methyl, ethyl, n-propyl, iso-propyl, n-butyl, iso-butyl, sec-butyl, tert-butyl, n-pentyl, sec-pentyl, tert-pentyl, n-hexyl, n-heptyl, n-octyl, 2-ethylhexyl, n-nonyl, iso-nonyl, 2-propylheptyl, n-decyl, n-dodecyl, n-tridecyl, iso-tri-decyl, n-tetradecyl, n-hexydecyl, n-octadecyl and eicosyl.

Combinations of the repeating units may be used.

Turning now to repeating unit B, it is repeating unit comprising at least one hydrophobic moiety. Thus, repeating unit B may be any polymerizable repeating unit that exhibits hydrophobic character, or another polymer having been functionalized with one or more hydrophobic moieties. Within the context of radical polymerization, repeating unit B may be any functionalized and unfunctionalized: (meth)acrylates, (meth)acrylamides, styrenes, 4-vinyl-1,2,3-triazoles, 5-vinyl-1,2,3-triazoles, vinyls, allyls, maleic anhydrides, fumarates, maleates, maleimides, α-β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, and/or allyl ethers.

Examples of hydrophobic alpha-olefins include isobutene, diisobutene, butene, pentene, hexene and additional olefins having 5 or more carbon atoms or mixtures thereof, such as, for example, 1-decene, 1-dodecene, 1-tetradecene, 1-hexadecene, 1-octadecene, 1-eicosene, 1-docosene, 1-tetracosene and 1-hexacosene. The hydrophobic alpha-olefin may be a $C_{22}$-alpha-olefin, a mixture of $C_{20}$-$C_{24}$-alpha-olefins and polyisobutene with, on average, 12 to 100 carbon atoms.

Further examples of hydrophobic repeating units B are known, including the (meth)acrylate and (meth)acrylamide families of repeating units. Includes in these classes are those repeating units represented by the structure:

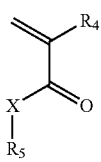

wherein
R₄ is selected from the group consisting of hydrogen, methyl, and combinations thereof,
R₅ is selected from the group consisting of functionalized and unfunctionalized alkyl, alkoxy, cycloalkyl, alkenyl, and aryl, and
X is selected from the group consisting of O, NH, and combinations thereof.

Non-limiting examples of hydrophobic (meth)acrylates include: ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, 2-naphthyl methacrylate, 2,2,3,3-tetrafluoropropyl methacrylate, 1,1,1,3,3,3-hexafluoroisopropyl methacrylate, 2,2,2-trifluoroethyl methacrylate, 2,2,3,3,3-pentafluoropropyl methacrylate, 2,2,3,4,4,4-hexafluorobutyl methacrylate, 2,2,3,3,4,4,4-heptafluorobutyl methacrylate, 2,2,3,3,4,4,5,5-octafluoropentyl methacrylate, 3,3,4,4,5,5,6,6,7,7,8,8,8-tridecafluorooctyl methacrylate, and 3,3,4,4,5,5,6,6,7,7,8,8,9,9,10,10,10-heptadecafluorodecyl methacrylate.

Hydrophobic repeating units B also are provided when X is NH. As with the (meth)acrylates, in particular embodiments R₅ may comprise 2 or more carbon atoms, and more particularly, from about 4 to about 50 or even more carbon atoms, and yet more particularly from about 4 to 30 carbon atoms. Non-limiting examples of hydrophobic (meth)acrylamides include: ethyl(meth)acrylamide, butyl(meth)acrylamide, hexyl(meth)acrylamide, 2-ethylhexyl(meth)acrylamide, octyl(meth)acrylamide, lauryl(meth)acrylamide, isobutyl(meth)acrylamide, isodecyl(meth)acrylamide, phenyl(meth)acrylamide, decyl(meth)acrylamide, 3,3,5-tri(methyl)cyclohexyl(meth)acrylamide, benzyl(meth)acrylamide, cyclohexyl(meth)acrylamide, stearyl(meth)acrylamide, tert-butyl(meth)acrylamide, tridecyl(meth)acrylamide, 2-naphthyl(meth)acrylamide, 2,2,3,3-tetrafluoropropyl(meth)acrylamide, 1,1,1,3,3,3-hexafluoroisopropyl(meth)acrylamide, 2,2,2-trifluoroethyl (meth)acrylamide, 2,2,3,3,3-pentafluoropropyl(meth) acrylamide, 2,2,3,4,4,4-hexafluorobutyl(meth)acrylamide, 2,2,3,3,4,4,4-heptafluorobutyl(meth)acrylamide, 2,2,3,3,4,4,5,5-octafluoropentyl(meth)acrylamide, 3,3,4,4,5,5,6,6,7,7,8,8,8-tridecafluorooctyl(meth)acrylamide, and 3,3,4,4,5,5,6,6,7,7,8,8,9,9,10,10,10-heptadecafluorodecyl(meth) acrylamide.

The invention embraces other hydrophobic repeating units, such as the styrene family of repeating units. Non-limiting examples thereof include the following: 1-vinyl naphthalene, 2-vinyl naphthalene, α-methyl styrene, 3-methyl styrene, 4-propyl styrene, t-butyl styrene, 4-cyclohexyl styrene, 4-dodecyl styrene, 2-ethyl-4-benzyl styrene, and 4-(phenyl butyl)styrene.

Examples of hydrophobic alkyl vinyl ethers that may be used as repeating unit B include methyl vinyl ether, ethyl vinyl ether, iso-propyl vinyl ether, n-butyl vinyl ether, iso-butyl vinyl ether, sec-butyl vinyl ether, octyl vinyl ether, decyl vinyl ether, dodecyl vinyl ether, hexadecyl vinyl ether, octadecyl vinyl ether, and combinations thereof.

It was mentioned earlier that the hydrophobic repeating unit B may be a repeating unit that is functionalized to impart hydrophobic character. Such functionalization includes those reactions to graft, add, or substitute one or more hydrophobic moieties to the repeating unit or polymer. To help illustrate this point, a suitable hydrophobic repeating unit B may be attained by reacting a polymerizable anhydride with a compound having at least one moiety that is reactive to the anhydride. The anhydride may be maleic anhydride, methyl maleic anhydride, dimethyl maleic anhydride, itaconic anhydride, citraconic anhydride, and tetrahydrophthalic anhydride, as well as their functionalized analogues. The moiety reactive to the anhydride may be a hydroxyl, amine, or thiol moiety so that a hydrophobically-modified anhydride results. The hydrophobic moiety may be any functionalized or unfunctionalized alkylene, alkyleneoxy, cycloalkylene, alkenylene, arylene with or without heteroatoms, and combinations thereof. Particularly, the hydrophobic moiety may comprise 2 to 50 carbon atoms, more particularly from 2 to 20 carbon atoms. The modification may be realized through the hydrophobic modification of the pre-polymerized repeating unit, or after polymerization with intact reactive groups on the polymer.

Polymers of the invention are polymerized from at least a repeating unit C that is chosen in order to modulate the polymer's properties as appropriate. Monomer C may be hydrophobic, hydrophilic, or amphiphilic; combinations may be used. One or more repeating unit C may be selected from the group consisting of functionalized and unfunctionalized: (meth)acrylates, (meth)acrylamides, styrenes, 4-vinyl-1,2,3-triazoles, 5-vinyl-1,2,3-triazoles, vinyls, allyls, maleic anhydrides, fumarates, maleates, maleimides, α-β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, and combinations thereof. One skilled in the art understands how to polymerize these repeating units with repeating units A and B, e.g., radical, emulsion, cationic, anionic polymerization methods.

In one non-limiting example, repeating unit C is an amide, and may be an N-vinyl amide represented by the structure:

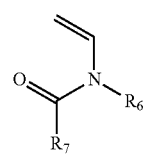

wherein R₆ and R₇ are selected from the group consisting of functionalized and unfunctionalized alkyl, alkoxy, cycloalkyl, alkenyl, and aryl groups, and where R₆ and R₇ may form a ring having from 5 to 7 carbon atoms.

In one embodiment, R₆ and R₇ may be independently selected from the group consisting of hydrogen and methyl. Examples of repeating unit C in this embodiment may include repeating units represented by the structure:

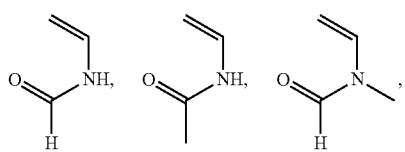

and combinations thereof.

Alternatively, R_6 and R_7 may form a ring structure, and repeating unit C may be represented by the structure:

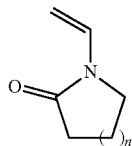

where n is an integer from 1 to 3. Examples of such repeating units include those having the structures:

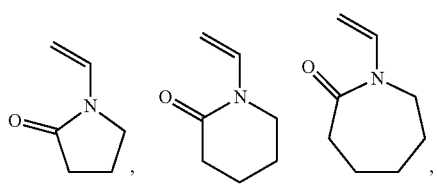

and combinations thereof.

In another embodiment, repeating unit C may be a (meth)acrylate and/or (meth)acrylamide, such as those described earlier for repeating unit B except repeating unit C does not have to be hydrophobic.

Other examples of repeating unit C include, without limitation:

(1)

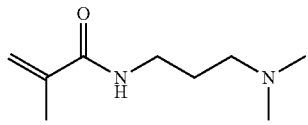

(2)

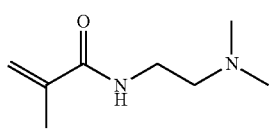

(3)

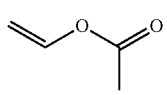

(4)

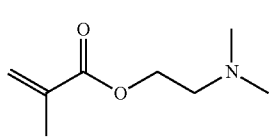

(5)

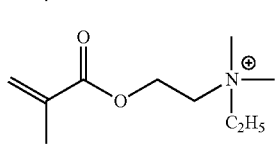

-continued (6)

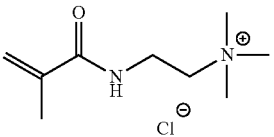

(7)

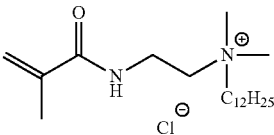

(8)

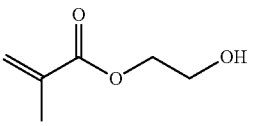

(9)

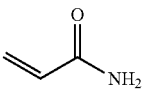

(10)

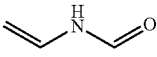

(11)

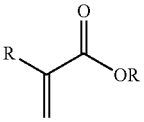

(12)

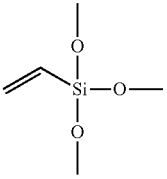

(13)

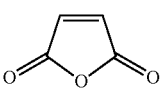

(14)

(15)

(16)

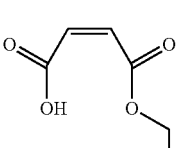

(17)

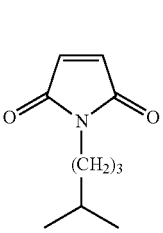

-continued

(18) 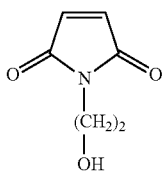

(19) 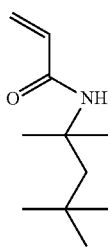

(20) 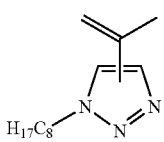

(21) 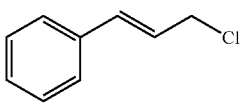

(22) 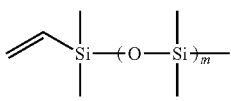

(23) 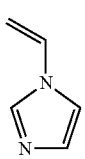

(24) 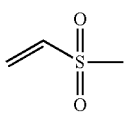

(25) 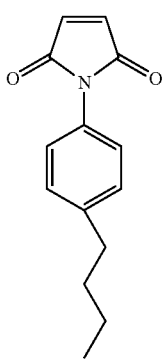

(26) 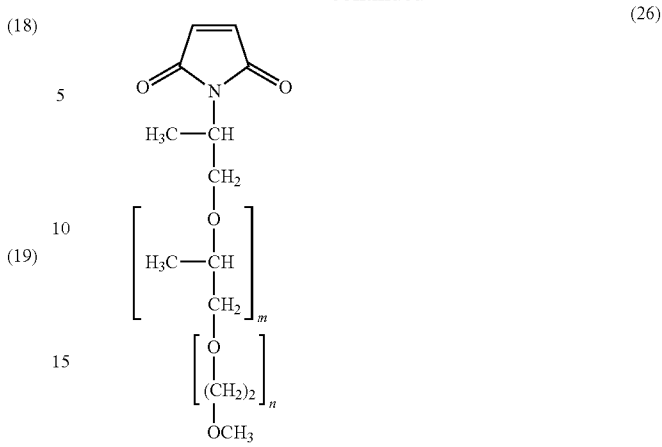

wherein each R is independently selected from the group consisting of hydrogen, and functionalized and unfunctionalized alkyl, cycloalkyl, alkenyl, and aryl groups, wherein any of the beforementioned groups may be with or without heteroatoms, and m and n are integers greater than or equal to 1.

Combinations of repeating units A, B, and/or C may be used (i.e., the multifunctional polymer may be a terpolymer, a tetrapolymer, or comprise more than 4 repeat units).

In addition to radical polymerization, polymers embraced by the invention include those synthesized by condensation polymerization. Maintained in this aspect of the invention are the descriptions of repeating units A (comprises a pseudo-cationic moiety), B (comprises a hydrophobic moiety), and repeating unit C. Polymers having a weight-average molecular weight of less than about 10,000 Da can be made by either radical or condensation polymerization methods; the slower reaction rate for condensation may allow better control of the final polymer properties.

Next, a brief description is provided for the repeating units when the multifunctional polymer is a condensation polymer.

Monomer A may be any multifunctional compound comprising at least one pseudo-cationic moiety and at least two reactive groups suitable for condensation polymerization. Examples of these reactive groups include, but are not limited to, hydroxyl and thiol groups. The pseudo-cationic moiety may comprise a nitrogen atom, such as amino or comprise a nitrogen or phosphorus heterocyclic ring. Examples of nitrogen heterocyclic rings include lactamyl, pyridinyl, imidazolyl, and pyrazolyl moieties. Typical condensation repeating units A may have the structure:

$$X-Q_2-X$$

wherein $Q_2$ is selected from the group consisting of functionalized and unfunctionalized alkylene, cycloalkylene, alkylene-oxy, alkenylene, and arylene, wherein $Q_2$ comprises one or more pseudo-cationic moieties pendant to or part of the final polymer backbone;

each X is independently selected from the group consisting of O and SH; and

Examples of condensation repeating units A include, but are not limited to:

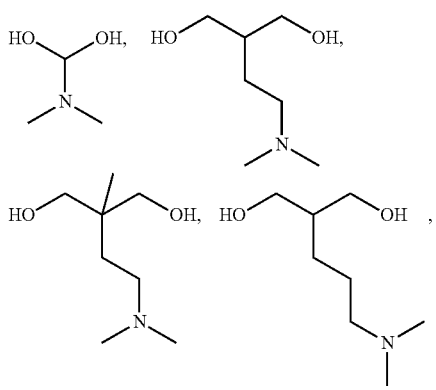

and combinations thereof.

Condensation repeating units B are those repeating units comprising at least one hydrophobic moiety, which may be pendant to or part of the final polymer backbone. In one embodiment, condensation repeating unit B is a polymerizable condensation repeating unit also having at least two reactive groups suitable for condensation polymerization. The hydrophobic group may or may not be pendant to the final polymer backbone. Such condensation repeating units B may have the structure:

$$X-Q_3-X$$

wherein
$Q_3$ is selected from the group consisting of functionalized and unfunctionalized alkylene, cycloalkylene, alkyleneoxy, alkenylene, and arylene, wherein $Q_3$ comprises one or more hydrophobic moieties pendant to or part of the final polymer backbone;
each X is independently selected from the group consisting of O and SH; and
Examples of condensation repeating units B include, but are not limited to:

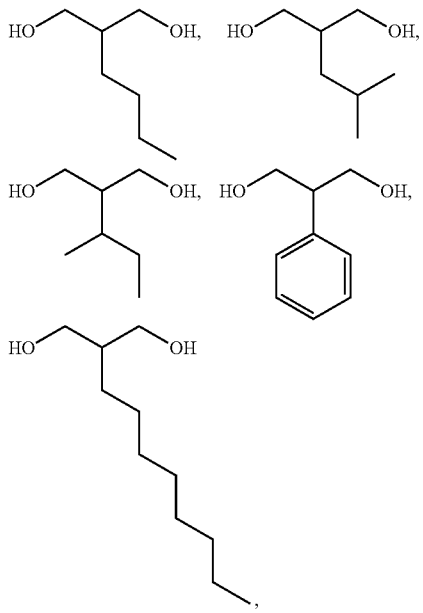

and combinations thereof.

Alternatively, the condensation repeating unit B is not a polymerizable condensation repeating unit per se, yet still repeats more than one throughout the polymer. The hydrophobic moiety may be provided by end-capping or grafting one or more hydrophobic moieties onto a condensation polymer. Such reactions are known to one skilled in the art, and may be accomplished, e.g., by reacting a polymer bearing reactive hydroxyl or amino groups with a compound having the structure:

$$R^*-W$$

wherein
R* is a hydrophobic moiety selected from the group consisting of alkyl, alkoxyl, cycloalkyl, alkenyl, and aryl, wherein any of the beforementioned groups may be with or without one or more heteroatoms, and
W is halogen,
under alkaline conditions (for example, with NaOH addition).

Multifunctional polymers that are condensation polymers also comprise repeating unit C, which can be any functional repeating unit having the structure:

$$X-Q_4-X$$

wherein
$Q_4$ is selected from the group consisting of functionalized and unfunctionalized alkylene, cycloalkylene, alkyleneoxy, alkenylene, and arylene;
each X is independently selected from the group consisting of O and SH; and
Non-limiting examples of condensation repeating units C include the following compounds:

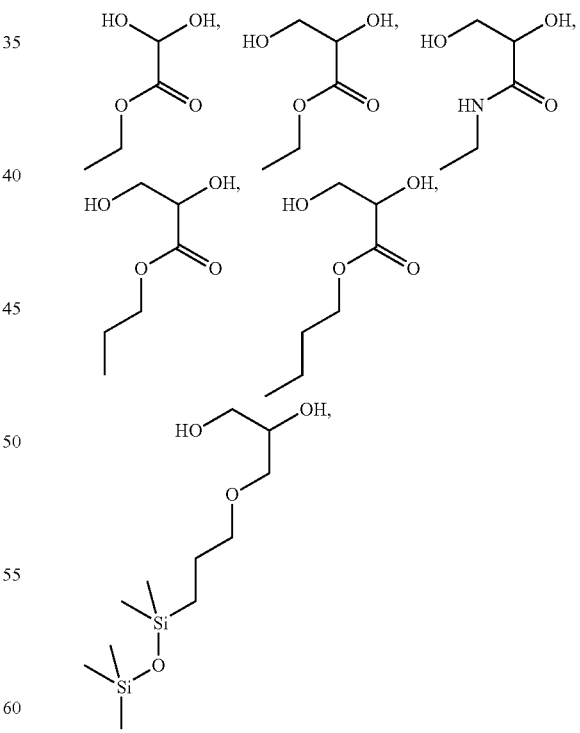

and combinations thereof.

Also suitable are polyetheramines, such as those based on propylene oxide and/or ethylene oxide, such as those sold into commercial sale under the trade name "Jeffamine" by The Huntsman Corporation.

Condensation multifunctional polymers may be prepared by reacting repeating units A, B, and C in the presence of one or more hydrocarbyl compounds having at least two halogens:

W-Q*W wherein

Q* is functionalized and unfunctionalized hydrocarbylene optionally having one or more heteroatoms, and each W is independently selected halogen.

A non-limiting reaction scheme illustrating condensation multifunctional polymers is given by:

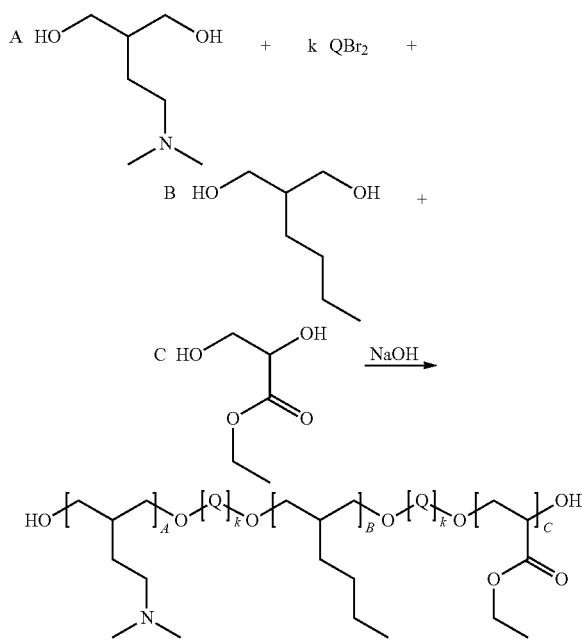

wherein A, B, C, and k represent the molar quantities of each reactant type. The silicone-containing compound is disclosed in *Journal of the American Chemical Society*, 1959, vol. 81, p. 2632.

As mentioned earlier, the reactive hydroxyl and amine groups may be subject to one or more further reactions, e.g., to produce an end-capped or grafted condensation polymer.

Additionally, multifunctional polymers comprising repeating units A, B, and C may be prepared by ring-opening polymerization of functionalized and unfunctionalized cyclic compounds. For example, monomer A may be a functionalized ethylene oxide having a pseudo-cationic moiety, such as:

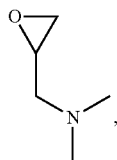

monomer B may be a functionalized ethylene oxide having at least one hydrophobic moiety, such as:

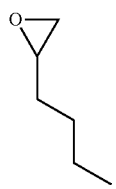

and monomer C may be any functionalized or unfunctionalized ethylene oxide, such as:

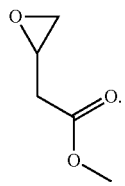

Other functionalized and unfunctionalized cyclic compounds with and without heteroatoms, including oxetanes, tetrahydrofurans, oxazines, and oxazolines, may be polymerized to yield corresponding multifunctional polymers according to the invention.

In one embodiment, the multifunctional polymer comprising repeating units A, B, and C may be a terpolymer, whether it be a radical polymerization polymer or a condensation polymer. It may be represented as:

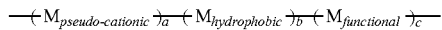

wherein:

said $M_{pseudo\text{-}cationic}$ is a repeating unit comprising at least one pseudo-cationic moiety, said $M_{hydrophobic}$ is a repeating unit comprising at least one hydrophobic moiety, said $M_{functional}$ is a functional repeating unit, and wherein said a, b, and c are molar ratios totaling 100%.

The reader will recognize that $M_{pseudo\text{-}cationic}$ is repeating unit A, $M_{hydrophobic}$ is repeating unit B, and $M_{functional}$ is repeating unit C as described earlier. For brevity, non-limiting descriptions for these repeating units will be understood to apply for terpolymer embodiments.

An aspect of this embodiment is a multifunctional radical polymerization polymer represented by the structure:

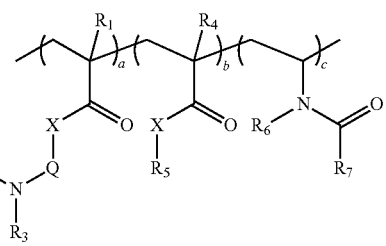

wherein:

$R_1$, $R_4$, and $R_5$ are independently selected from the group consisting of functionalized and unfunctionalized alkyl, alkoxy, cycloalkyl, alkenyl, and aryl groups;

$R_2$ and $R_3$ are $C_1$-$C_5$ alkyl groups, $R_6$ and $R_7$ are independently selected from the group consisting of functionalized and unfunctionalized alkyl, alkoxy, cycloalkyl, alkenyl, and aryl groups, and $R_6$ and $R_7$ may form a 5 to 7-membered ring, X is O or NH or combinations thereof, Q is selected from the group consisting of functionalized and unfunctionalized alkylene, alkyleneoxy, cycloalkylene, alkenylene, and arylene groups, and and the subscripts a, b, and c refer to the molar amounts of the three repeating units.

The invention embraces various embodiments with regard to generic substituent. For example, in various aspects Q may be $C_1$-$C_5$ alkylene, more particularly $C_1$-$C_4$ alkylene; or yet more particularly propylene. Various aspects of $R_5$ include $C_3$-$C_{18}$ alkyl, more particularly $C_4$-$C_{16}$ alkyl, and yet more particularly $C_4$-$C_{12}$ alkyl. $R_1$ and $R_4$ may be hydrogen or methyl; more particularly, they are methyl. In one aspect, $R_2$ and $R_3$ may be $C_1$-$C_3$ alkyl; more particularly $C_1$-$C_2$ alkyl; and yet more particularly methyl. Regarding the molar subscripts, a may range from about 5% to about 80%, b may range from about 5% to about 60%, and c may range from about 5% to about 80%. More particularly, a may range from about 10% to about 70%, b may range from about 15% to about 50%, and c may range from about 10% to about 70%. In one aspect, the weight-average molecular weight of the polymer may be less than 10,000 Da.

In one of the terpolymer embodiments, the invention provides amphiphilic, pseudo-cationic multifunctional polymers. The multifunctional polymers may be prepared by a polymerization of: (A) a pseudo-cationic vinyl repeating unit such as N-[2-(dimethylamino)ethyl](meth)acrylamide, N-[3-(dimethylamino)propyl] (meth)acrylamide, or N-[4-(dimethylamino)butyl] (meth)acrylamide; with (B) a hydrophobic vinyl repeating units; such as methyl(meth)acrylate, ethyl(meth)acrylate, or butyl(meth)acrylate, and (C) N-vinyl amide repeating unit; such as N-vinyl formamide, N-methyl-N-vinyl formamide, N-vinyl pyrrolidone, and/or N-vinyl caprolactam. In one aspect, the polymer may be represented by the structures:

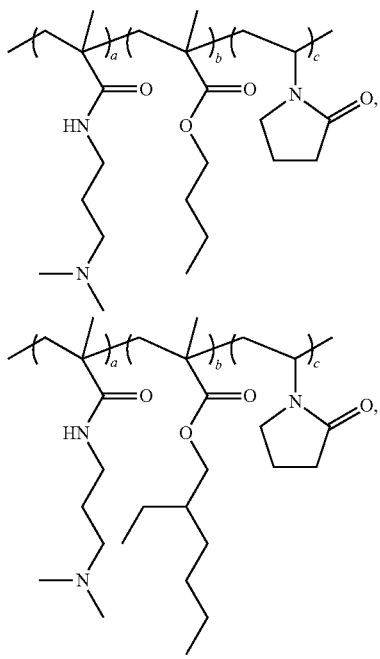

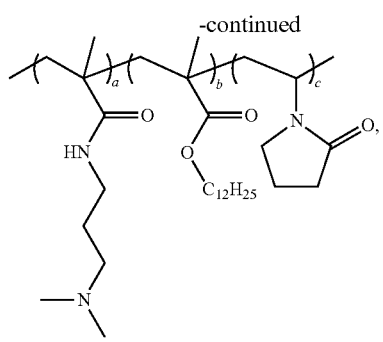

wherein a, b, and c are as defined above.

Also embraced by the invention is a method of providing antimicrobial activity in or on a composition, wherein the method comprising the step: contacting a composition with at least one multifunctional polymer synthesized from at least repeating unit types: a first repeating unit A comprising at least one pseudo-cationic tertiary amine, a second repeating unit B that is hydrophobic, and a third repeating unit C. Separately, the weight-average molecular weight of the polymer may be less than about 10,000 Da. The molecular weight may be chosen, in part, based on the addition level of the multifunctional polymer, multifunctional polymer type, rheology considerations, and desired level of antimicrobial activity. Descriptions of the method's repeating units A, B, and C mirror the description provided earlier, and for the sake of brevity are not repeated here.

In one embodiment, the method's polymer may be a terpolymer, and may be represented as:

wherein:

said $M_{pseudo\text{-}cationic}$ is a repeating unit comprising at least one pseudo-cationic moiety, said $M_{hydrophobic}$ is a repeating unit comprising at least one hydrophobic moiety, said $M_{functional}$ is a functional repeating unit, and wherein said a, b, and c are molar ratios totaling 100%.

Particularly but without limitation, the polymer may be represented by the structure:

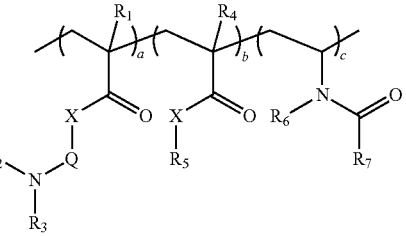

wherein:

$R_1$, $R_4$, and $R_5$ are independently selected from the group consisting of functionalized and unfunctionalized alkyl, alkoxy, cycloalkyl, alkenyl, and aryl groups;

$R_2$ and $R_3$ are $C_1$-$C_5$ alkyl groups, $R_6$ and $R_7$ are independently selected from the group consisting of functionalized and unfunctionalized alkyl, alkoxy, cycloalkyl, alkenyl, and aryl groups, and $R_6$ and $R_7$ may form a 5 to 7-membered ring, X is O or NH or combinations thereof, Q is selected from the group consisting of functionalized and unfunctionalized alkylene, alkyleneoxy, cycloalkylene, alkenylene, and arylene groups, and and the subscripts a, b, and c refer to the molar amounts of the three repeating units.

Non-limiting examples of polymers that may be used in the method include:

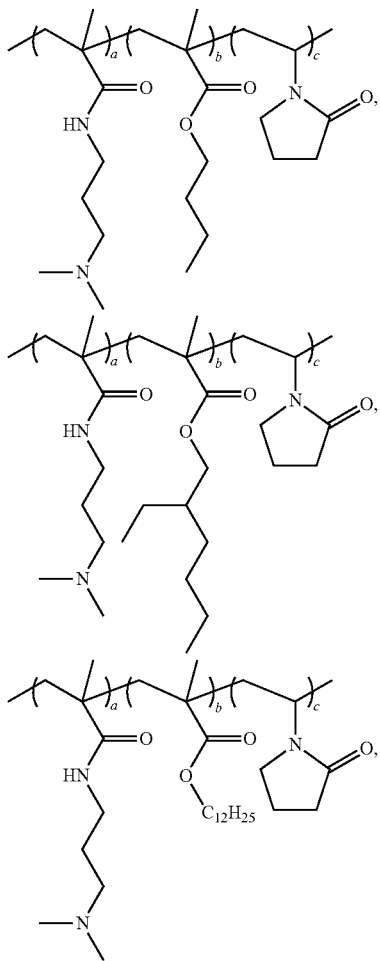

wherein a, b, and c are as defined above.

The aforementioned method comprises the step, "contacting a composition with a multifunctional polymer" meaning that the composition may be molecular blend, a nano/micro/macroscopic dispersion, and/or nano/micro/macroscopic emulsion with one or more multifunctional polymer(s). Additionally, the composition may contact one or more multifunctional polymer(s) at an interface, e.g., as a film, in one or more layers, and/or along a phase boundary.

In one embodiment, the method provides antimicrobial activity against a microbe selected from the group consisting of *S. aureus, E. coli, P. aeruginosa, A. niger, C. albicans*, and combinations thereof. In a separate embodiment, the multifunctional polymers express antimicrobial activity at a microorganism concentration of $10^5$-$10^6$ cfu/mL and a polymer concentration of 1% (w/w) or greater.

The polymers may be designed to have a wide variety of physical and mechanical properties, to suit a particular application. The polymers may be random, block, or alternating polymers, or combinations thereof. The properties of the multifunctional polymers can be further designed by appropriate selection of the type of the vinyl repeating units employed, the ratios of the vinyl repeating units employed, and the weight-average molecular weight of the resulting polymer.

In another aspect, a wide variety of compositions comprising the modified polymers are provided, including adhesives, aerosols, agricultural compositions, beverages, biocides, cleaning compositions, coating compositions, cosmetic compositions, dental compositions, detergents, drugs, electronics, encapsulations, foods, hair sprays, household-industrial-institutional (HI&I), inks, lithographic solutions, membrane compositions, metal fluids, oilfield compositions, paints, paper, personal care compositions, pharmaceuticals, plasters, plastics, printing, and wood-care compositions.

Polymers of the invention may be used in a wide variety of compositions such as in adhesives, agricultural, biocides, coatings, electronics, household-industrial-institutional (HI&I), inks, membranes, metal fluids, oilfield, paper, paints, plastics, printing, plasters, and wood-care compositions.

Depending on the end application, one or more fillers may be included in the compositions and may be added for improved rheological properties and/or stress reduction. Examples of suitable nonconductive fillers include alumina, aluminum hydroxide, silica, fused silica, fumed silica, vermiculite, mica, wollastonite, calcium carbonate, titania, sand, glass, barium sulfate, zirconium, carbon black, organic fillers, and halogenated ethylene polymers, such as, tetrafluoroethylene, trifluoroethylene, vinylidene fluoride, vinyl fluoride, vinylidene chloride, and vinyl chloride. Examples of suitable conductive fillers include carbon black, graphite, gold, silver, copper, platinum, palladium, nickel, aluminum, silicon carbide, boron nitride, diamond, and alumina. Combinations of these fillers may be used.

The filler particles may be of any appropriate size, particularly from the nano to micro range. The choice of such size for any particular end use is within the expertise of one skilled in the art. The filler may be present in an amount from about 10% to about 90% by weight of the total composition. More than one filler type may be used in a composition and the fillers may or may not be surface treated. Appropriate filler sizes can be determined by the practitioner, and, in particular, may be within the range from about 20 nm to about 100 μm.

Other materials, such as adhesion promoters (e.g. epoxides, silanes), dyes, pigments, and rheology modifiers may be added as desired for the modification of the final properties. Such materials and the amounts needed are within the expertise of those skilled in the art.

Compositions belonging to the personal care/cosmetic and pharmaceutical arts find utility in altering, delivering an active, enhancing, improving, modifying the appearance, condition, color, health, style of the skin (including face, scalp, and lips), hair, nails, and oral cavity. Many examples and product forms of these compositions are known. These compositions can impart benefits that include, but are not limited to, hair style flexibility, hair style durability, humidity resistance for hair, color and/or color protection, moisturization, wrinkle reduction, protection from ultraviolet radiation, water proofness, water resistance, wear resistance, thermal protection, adhesion, active ingredient delivery, anti-cavity, and/or anti-gingivitis protection. As such, these compositions are sometimes categorized in the following areas: skin care, hair care (both styling and non-styling), sun care, cosmetics (including color cosmetics), antiperspirants, deodorants, oral hygiene, and men's and women's personal hygiene/grooming. In some cases these benefits and care areas overlap with another.

Skin care compositions include those materials used on the body, face, hands, lips, and/or scalp, and are beneficial for many reasons, such as firming, anti-cellulite, moisturizing, nourishing, cleaning, reducing or eliminating the appearance of wrinkles or lentigo, toning, and/or purifying. They also can be used to sanitize.

Consumers can identify many of the compositions that serve the sun care area, for example after-fun, children's, beach, self-tan, sports (i.e., being sweat proof, waterproof, resistant to running, or having added UV absorbers and/or antioxidants), sensitive skin products (i.e., having low irritation to the eyes and/or skin, and/or being free of fragrances and/or dyes), daily wear, leave-on hair creams, lotions, styling products, and hair sprays. Typically, sun care products also comprise one or more UV actives, which are those organic and inorganic materials that scatter, absorb, and/or reflect radiation having a wavelength from about 100 nm to about 400 nm. In one aspect, the sun care product protects against UV-A and/or UV-B radiation. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin, which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns, which may be harmful. Alternatively, sun care products may omit UV actives, and may be regarded as a tanning oil or a tan promoter. Some sun care compositions may promote soothe skin after sun exposure, and/or be formulated for application to the lips, hair, or the area around the eyes. Self-tan compositions, which are products that color skin without requiring full sun exposure, also fit under the sun care umbrella. The many different sun care product formats include may assume a consistency ranging from liquid to semi liquid forms (e.g., milks, creams), to thicker forms like gels, creams, pastes, and even solid- and wax-like forms. Sun care products also may take the form of an aerosol, spray, mist, roll-on, or wipe.

Hair care compositions include shampoos, leave-on and rinse-out conditioners used for conditioning, moisturizing, repairing, hair colors, hair relaxers, and deep conditioners and treatments such as hot oils and waxes, 2-in-1 shampoo/conditioner combination products, 3-in-1 shampoo/conditioner/styling agent. The many types of hair care products can be delivered in an array of formats, including aerosol sprays, pump sprays, gel sprays, mousses, gels, waxes, creams, pomades, spritzes, putties, lacquers, de-frizzing serums, perms, relaxants and colorants.

Color cosmetic compositions include facial make-up, eye makeup, mascaras, lip and nail products. Facial make-up compositions include foundation (liquid, solid, and semi-solid)—skin tinted creams, liquid, sticks, mousses used as a base under make-up, rouge, face powder, blusher, highlighters, face bronzers, concealers, and 2-way cake products.

Personal care/cosmetics also include eye make-up, mascaras, eyeliners, eye shadows, eyebrow pencils and eye pencils. Lip products include lipsticks, lip pencils, lip gloss, transparent bases and tinted lip moisturizers as well as multi-function color sticks that also can be used for cheeks and eyes. Nail products include nail varnishes/enamels, nail varnish removers, treatments, home-manicure products such as cuticle softeners and nail strengtheners.

In addition to the skin, hair, and sun care compositions summarized above, the polymers related herein also find application in oral care compositions. Non-limiting examples or oral care compositions include toothpastes (including toothpaste gels), denture adhesives, whiteners, anesthetics, and dental floss and related products. These compositions may take any product format, such as pastes, gels, creams, solutions, dispersions, rinses, flosses, aerosols, powders, and lozenges.

Grooming products for men and women include shaving products and toiletries, which may find use in preparing the skin and/or hair for dry or wet shaving. In addition, these compositions may help to moisturize, cool, and/or soothe skin. A variety of product forms are known, a few of which are foams, gels, creams, sticks, oils, solutions, tonics, balms, aerosols, mists, sprays, and wipes.

The polymer also can be used in other personal care/cosmetic applications, such as an absorbent material in appropriate applications such as diapers, incontinence products, feminine products, and other related products.

The polymers described herein also find application in bath and shower compositions, such as foams, gels, salts, oils, balls, liquids, powders and pearls. Also included are bar soaps, body washes, shower gels, cleansers, gels, oils, foams, scrubs and creams. As a natural extension of this category, these compositions also include liquid soaps and hand sanitizers used for cleaning hands.

The polymer of the invention can be used in combination with one or more additional personal care/cosmetically acceptable additives chosen from, for example, conditioning agents, protecting agents, such as, for example, hydrosoluble, liposoluble and water-insoluble UV filters, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, hydroxy acids, various cationic, anionic and nonionic polymers, cationic and nonionic polyether associative polyurethanes, preservatives, vegetable oils, mineral oils, synthetic oils, polyols such as glycols and glycerol, silicones, aliphatic alcohols, colorants, bleaching agents, highlighting agents and sequestrants.

These additives may be present in the composition according to the invention in proportions that may range from about 0% to about 20% by weight in relation to the total weight of the composition. An expert in the field according to its nature and its function may easily determine the precise amount of each additive.

Examples of these co-ingredients and many others can be found in the following references, each of which is herein incorporated in its entirety by reference: "Inventory and common nomenclature of ingredients employed in cosmetic products," Official Journal of the European Union, 5.4.2006, pages L 97/1 through L 97/528; and International Cosmetic Ingredient Dictionary and Handbook, 13th edition, ISBN: 1882621476, published by The Personal Care Products Council in January 2010.

Any known conditioning agent is useful in the personal care/cosmetic compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin-altering agent is useful in the compositions of this invention. A few examples of conditioning agents include cationic polymers, cationic surfactants and cationic silicones. Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a number-average molecular weight, which falls between about 500 and 5,000,000, for example between 1000 and 3,000,000. Cationic polymers may be chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as:

a. homopolymers and copolymers derived from acrylic or methacrylic esters or amides. The copolymers can contain one or more units derived from acrylamides, methacrylamides, diacetone acrylamides, acrylic or methacrylic acids or their esters, vinyl lactams such as vinyl pyrrolidone or vinyl caprolactam, and vinyl esters. Specific examples include: copolymers of acrylamide and N,N-dimethylaminoethyl methacrylate quaternized with dimethyl sulfate or with an alkyl halide; copolymers of acrylamide and methacryloyloxyethyl trimethyl ammonium chloride; the copolymer of acrylamide and methacryloyloxyethyl trimethyl ammonium methosulfate; copolymers of vinyl pyrrolidone/dialkylaminoalkyl acrylate or methacrylate, optionally quaternized, such as the products sold under the name Gafquat® by Ashland Specialty Ingredients; the N,N-dimethylaminoethyl methacrylate/vinyl caprolactam/vinyl pyrrolidone terpolymers, such as the product sold under the name Gaffix® VC 713 by Ashland Specialty Ingredients; the vinyl pyrrolidone/methacrylamidopropyl dimethylamine copolymer, marketed under the name Styleze® CC-10 by Ashland Specialty Ingredients; the vinyl pyrrolidone/quaternized dimethyl amino propyl methacrylamide copolymers such as the product sold under the name Gafquat® HS-100 by Ashland Specialty Ingredients; and the vinyl pyrrolidone/dimethylaminopropyl methacrylamide/$C_9$-$C_{24}$ alkyldimethylaminopropyl methacrylic acid quaternized terpolymers described in U.S. Pat. No. 6,207,778 and marketed under the name Styleze® W-20 by Ashland Specialty Ingredients.

b. derivatives of cellulose ethers containing quaternary ammonium groups, such as hydroxyethyl cellulose quaternary ammonium that has reacted with an epoxide substituted by a trimethyl ammonium group.

c. derivatives of cationic cellulose such as cellulose copolymers or derivatives of cellulose grafted with a hydrosoluble quaternary ammonium repeating unit, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

d. cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

e. polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

f. water-soluble polyamino amides prepared by polycondensation of an acid compound with a polyamine. These polyamino amides may be reticulated.

g. derivatives of polyamino amides resulting from the condensation of polyalkylene polyamines with polycarboxylic acids followed by alkylation by bi-functional agents.

h. polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.

i. the cyclopolymers of alkyl diallyl amine or dialkyl diallyl ammonium such as the homopolymer of dimethyl diallyl ammonium chloride and copolymers of diallyl dimethyl ammonium chloride and acrylamide.

j. quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

k. quaternary polyammonium polymers, including, for example, Mirapol® A 15, Mirapol® AD1, Mirapol® AZ1, and Mirapol® 175 products sold by Miranol.

l. the quaternary polymers of vinyl pyrrolidone and vinyl imidazole such as the products sold under the names Luviquat® FC 905, FC 550, and FC 370 by BASF.

m. quaternary polyamines.

n. reticulated polymers known in the art.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl. Hydrolyzed proteins include Croquat™ L, in which the quaternary ammonium groups include a C12 alkyl group, Croquat™ M, in which the quaternary ammonium groups include C10-C18 alkyl groups, Croquat™ S in which the quaternary ammonium groups include a C18 alkyl group and Crotein Q in which the quaternary ammonium groups include at least one C1-C18 alkyl group. These products are sold by Croda. The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein.

The conditioning agent can be a ceramide type of compound such as a ceramide, a glycoceramide, a pseudoceramide, or a neoceramide. These compounds can be natural or synthetic. Compounds of the ceramide type are, for example, described in patents pending DE4424530, DE4424533, DE4402929, DE4420736, WO95/23807, WO94/07844, EP-A-0646572, WO95/16665, FR-2 673 179, EP-A-0227994, WO 94/07844, WO 94/24097, and WO 94/10131. Ceramide type compounds useful herein include 2-N-linoleoyl amino-octadecane-1,3-diol, 2-N-oleoyl amino-octadecane-1,3-diol, 2-N-palmitoyl amino-octadecane-1,3-diol, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counter-ion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine. The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic esters including mono-, di-, tri- and tetra-carboxylic acids.

The conditioning agent can be a fluorinated or perfluorinated oil. Fluorinated oils include perfluoropolyethers described in EP-A-486135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers. Of course, mixtures of two or more conditioning agents can be used.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, polymers, or gums. They may be volatile or non-volatile. The silicones can be selected from polyalkyl siloxanes, polyaryl siloxanes, polyalkyl aryl siloxanes, silicone gums and polymers, and polyorgano siloxanes modified by organofunctional groups, and combinations thereof. Suitable polyalkyl siloxanes include polydimethyl siloxanes with terminal trimethyl silyl groups or terminal dimethyl silanol groups (dimethiconol) and polyalkyl (C1-C20) siloxanes.

Suitable polyalkyl aryl siloxanes include polydimethyl methyl phenyl siloxanes and polydimethyl diphenyl siloxanes, linear or branched. The silicone gums suitable for use herein include polydiorganosiloxanes including those having a number-average molecular weight between 200,000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane. Suitable silicone polymers include silicones with a dimethyl/trimethyl siloxane structure and polymers of the trimethyl siloxysilicate type. The organo-modified silicones suitable for use in the invention include silicones such as those previously defined and containing one or more organofunctional groups attached by means of a hydrocarbon radical and grafted siliconated polymers. In one embodiment the silicones are amino functional silicones. The silicones may be used in the form of emulsions, nano-emulsions, or micro-emulsions.

The conditioning agent or agents can be present in an amount from about 0.001% to about 20%, particularly from about 0.01% to about 10%, and even more particularly from about 0.1% to about 3% by weight based on the total weight of the final composition. The personal care/cosmetic compositions of the invention can contain one or more protecting agents in combination with the above-described polymer to prevent or limit the degrading effects of natural physical and/or chemical assaults on the keratinous materials.

The protecting agent can be chosen from hydrosoluble, liposoluble and water-insoluble UV filters, antiradical agents, antioxidants, vitamins and pro-vitamins. The above-described cationic polymer enhances the deposition of these materials onto the hair or skin substrate enhancing protection of hair to UV damage. Organic UV filters (systems that filter out UV rays) can be chosen from among hydrosoluble or liposoluble filters, whether siliconated or nonsiliconated, and mineral oxide particles, the surface of which may be treated. Hydrosoluble organic UV filters may be chosen from para-amino benzoic acid and its salts, anthranilic acid and its salts, salicylic acid and its salts, hydroxy cinnamic acid and its salts, sulfonic derivatives of benzothiazoles, benzimidizoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and combinations thereof. Hydrophilic polymers, which have light-protective qualities against UV rays, can be used. These include polymers containing benzylidene camphor and/or benzotriazole groups.

Suitable liposoluble organic UV filters include derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silico-organic residues; esters of cinnamic acid; derivatives of camphor; derivatives of trianilino-s-triazine; the ethylic ester urocanic acid; benzotriazoles; derivatives of hydroxy phenyl triazine; bis-resorcinol-dialkyl amino triazine; and combinations thereof. The liposoluble (or lipophilic) organic UV filter can be chosen from octyl salicylate; 4-tert-butyl-4'-methoxy dibenzoyl methane; octocrylene; 4-methoxy cinnamate; 2-ethylhexyl[2-ethylhexyl 4-methoxycinnamate]; and 2-(2H-benzotriazol-2-yl)-4-methyl-6-[2-methyl-3-[1,3, 3,3-tetramethyl-1-[(trimethyl silyl)oxy]disiloxanyl]propynyl]phenol. Other UV filters that may be useful are derivatives of benzophenones such as 2-hydroxy-4-methoxy benzophenone-5-sulfonic acid, 2-hydroxy-4-methoxy benzophenone, derivatives of benzalmalonates such as poly dimethyl/methyl (3(4-(2,2-bis-ethoxy carbonyl vinyl)-phenoxy)-propenyl) siloxane, derivatives of benzylidene camphor such as beta-beta'camphosulfonic[1-4 divinylbenzene] acid and derivatives of benzimidazole such as 2-phenyl-benzimidazol-5-sulfonic acid. Water-insoluble UV filters include various mineral oxides. The mineral oxides may be selected from among titanium oxides, zinc oxides, and cerium oxides. The mineral oxides can be used in the form of ultrafine nanoparticles. For example, the UV filters can include Escalol® HP-610 (dimethylpabamido propyl laurdimonium tosylate and propylene glycol stearate) or Crodasorb HP (polyquaternium 59).

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP, vitamin A, and derivatives thereof. The provitamins can be selected from panthenol and retinol.

The protecting agent can be present in an amount from about 0.001% to about 20% by weight, particularly from about 0.01% to about 10% by weight, and more particularly from 0.1% to about 5% by weight of the total weight of the final composition.

The composition of the invention can contain a fixing agent in combination with the above-described polymer. The fixing agent can be an anionic polymer chosen from polymers containing carboxylic units derived from unsaturated carboxylic mono- or polyacids.

The fixing agent can be an amphoteric polymer chosen from the polymer containing recurring units derived from:
i. at least one co-repeating unit containing carboxylic acid units, and
ii. at least one basic co-repeating unit, such as esters with primary, secondary, tertiary, and quaternary amino substituents of acrylic and methacrylic acids and the product of quaternization of dimethylaminoethyl methacrylate with dimethyl or diethyl sulfate.

The fixing agent can be a nonionic polymer chosen from polyalkyloxazolines; vinyl acetate homopolymers; vinyl acetate and acrylic ester copolymers; vinyl acetate and ethylene copolymers; vinyl acetate and maleic ester copolymers; polyethylene and maleic anhydride copolymers; homopolymers of alkyl acrylates; homopolymers of alkyl methacrylates; copolymers of acrylic esters; copolymers of alkyl acrylates and alkyl methacrylates; copolymers of acrylonitrile and a nonionic repeating unit chosen from among butadiene and alkyl(meth)acrylates; copolymers of alkyl acrylate and urethane; and polyamides. The fixing agent can be a functionalized or unfunctionalized, silicone or non-silicone polyurethane. The fixing polymer can be a polymer of the grafted silicone type containing a polysiloxane portion and a portion consisting of a nonsilicone organic chain, with one of the two portions forming the main chain of the polymer, and with the other being grafted onto the main chain.

The fixing agent can be present in the composition in a relative weight concentration between about 0.1% to about 10%, for example, from about 0.5% to about 5%.

The personal care/cosmetic composition of the invention can contain an oxidizing agent in combination with the above-described polymer. The oxidizing agent can be chosen from the group of hydrogen peroxide, urea peroxide, alkali metal bromates, ferricyanides, persalts, and redox enzymes, optionally with their respective donor or cofactor. For example, the oxidizing agent can be hydrogen peroxide. The oxidizing agent can be a solution of oxygenated water whose titer varies from 1 to 40 volumes.

The personal care/cosmetic composition of the invention can contain at least one reducing agent in combination with the above-described polymer in amounts from about 0.01% to about 30%, particularly from about 0.05% to about 20% of the total weight of the composition. The reducing agents can be selected from thiols, like cysteine, thioglycolic acid, thiolactic acid, their salts and esters, cysteamine, and its salts or sulfites. In the case of compositions intended for bleaching, ascorbic acid, its salts and its esters, erythorbic acid, its salts and its esters, and sulfinates, like sodium hydroxymethanesulfinate can be used.

The personal care/cosmetic composition of the invention can contain a dye in combination with the above-described polymer. The dye can be selected from the group consisting of neutral acid or cationic nitrobenzene dyes, neutral acid or cationic azo dyes, quinone dyes, neutral, acid or cationic anthraquinone dyes, azine dyes, triarylmethane dyes, indoamine dyes and natural dyes. The dye or dyes can be present in a concentration from about 0.001% to about 20%, and particularly from about 0.005% to about 10% based on the total weight of the composition.

In addition, the personal care/cosmetic compositions can include at least one surfactant in combination with the above-described polymer. The surfactant can be present in an amount from about 0.1% to about 60%, particularly from about 1% to about 40%, and more particularly from about 5% to about 30% by weight based on the total weight of the composition. The surfactant may be chosen from among anionic, amphoteric, or non-ionic surfactants, or mixtures of them known to be useful in personal care/cosmetic compositions.

One or more suitable thickeners or viscosity increasing agents may be included in combination with the above-described polymer in the personal care/cosmetic compositions of the invention. Suitable thickeners and/or viscosity increasing agents include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; *alcaligenes* polysaccharides; algin; alginic acid; almondamide DEA; almondamidopropyl betaine; aluminum/magnesium hydroxide stearate; ammonium acrylates/ acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; *astragalus gummifer* gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; coco-betaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; *phaseolus angularis* seed powder; polianthes tuberosa extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa* multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *zea mays* (corn) starch; and blends thereof.

In one such embodiment, the thickeners or viscosity increasing agents include carbomers, Aculyn™ and Stabileze®, e.g., crosslinked acrylic acid, crosslinked poly(methylvinyl ether/maleic anhydride) copolymer, acrylamides, carboxymethyl cellulose, and the like.

The personal care/cosmetic composition of the invention can contain at least one amphoteric polymer or a cationic polymer in combination with the above-described polymer. The cationic or amphoteric polymer or polymers can be present in an amount from about 0.01% to about 10%, particularly from about 0.05% to about 5%, and more particularly from about 0.1% to about 3% by weight of the total weight of the composition.

For some embodiments, it may be preferred to add one or more preservatives and/or antimicrobial agents, such as, but not limited to, benzoic acid, sorbic acid, dehydroacetic acid, piroctone olamine, DMDM hydantoin, IPBC, triclosan, bronopol, formaldehyde, isothiazolinones, nitrates/nitrites, parabens, phenoxyethanol, potassium sorbate, sodium benzoate, sulphites, and sulphur dioxide. Combinations of preservatives may be used.

In other embodiments it may be desirable to incorporate preservative boosters/solvents, select examples of which include caprylyl glycol, hexylene glycol, pentylene glycol, ethylhexylglycerin, caprylhydroxamic acid, and glyceryl caprylate.

In other embodiments it may be desirable to include one or more other ingredients, such as synthetic and natural oils and waxes. The synthetic oils include polyolefins, e.g., poly-α-olefins such as polybutenes, polyisobutenes and polydecenes. The polyolefins can be hydrogenated. The mineral oils suitable for use in the compositions of the invention include hexadecane and oil of paraffin. Suitable animal and vegetable oils include sunflower, corn, soy, avocado, jojoba, squash, raisin seed, sesame seed, walnut oils, fish oils, glycerol tricaprocaprylate, Purcellin oil or liquid jojoba. Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot. Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax.

The personal care/cosmetic compositions may be used to wash and treat keratinous material such as hair, skin, eyelashes, eyebrows, fingernails, lips, and hairy skin. The invention provides a method for treating keratinous material including the skin or hair, by applying to skin or keratinous materials a personal care/cosmetic composition as described above, and then eventually rinsing it with water. Accordingly, the method makes it possible to maintain the hairstyle, treatment, care, washing, or make-up removal of the skin, the hair, and any other keratinous material.

The personal care/cosmetic compositions described herein are useful in personal care/cosmetic products, including, but not limited to, gels, lotions, glazes, glues, mousses, sprays, fixatives, shampoos, conditioners, 2-in-1 shampoos, temporary hair dyes, semi-permanent hair dyes, permanent hair dyes, straighteners, permanent waves, relaxers, creams, putties, waxes, pomades, moisturizers, mascaras, lip balms and foam enhancers. The personal care/cosmetic compositions can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from about 4% to about 50% by weight, particularly from about 6% to about 35% by weight, and even more particularly from about 8% to about 25% by weight of the total weight of the final composition. The personal care/cosmetic compositions may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process. The personal care/cosmetic compositions may also take the form of skin-washing compositions, and particularly in the form of solutions or gels for the bath or shower, or of make-up removal products. The personal care/cosmetic compositions may also be in the form of aqueous or hydro-alcoholic solutions for skin and/or hair care.

The pH of the composition applied to the keratinous material is generally between 2 and 12. In one embodiment, the pH is from about 3 to about 8, and may be adjusted to the desired value by means of acidifying or alkalinizing agents that are well known in the state of the art. Thus, the composition of the invention can contain at least one alkalizing or acidifying agent in amounts from about 0.01% to about 30% based on the total weight of the composition.

The alkalizing agent can be chosen from ammonia, alkali hydroxides, alkali carbonates, alkanolamines, like mono-, di- and triethanolamines, as well as their derivatives, hydroxyalkylamines and ethoxylated and/or propoxylated ethylenediamines, unsubstituted and substituted propylenediamines The acidifying agent can be chosen from mineral or organic acids, like hydrochloric acid, orthophosphoric acid, carboxylic acids like tartaric acid, citric acid, or lactic acid, or sulfonic acids, and the like.

The personal care/cosmetic compositions of the invention may include a physiological and cosmetically acceptable medium. Such medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers. Alternatively, the personal care/cosmetic compositions can be anhydrous.

Generally, personal care/cosmetic compositions can be prepared by simple mixing procedures well known in the art.

The invented polymers can be prepared according to the examples set out below. The examples are presented for purposes of demonstrating, but not limiting, the preparation of the compounds and compositions of this invention.

EXAMPLES

The following non-limiting examples are provided to illustrate a few methods for preparing multifunctional polymers.

Example 1

Synthesis of 16% N-(3-Dimethylaminopropyl) Methacrylamide/20% Butyl Methacrylate/64% N-vinyl Pyrrolidone (Molar Ratios) Terpolymer

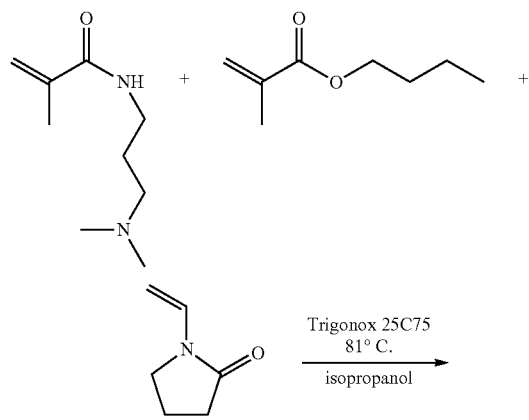

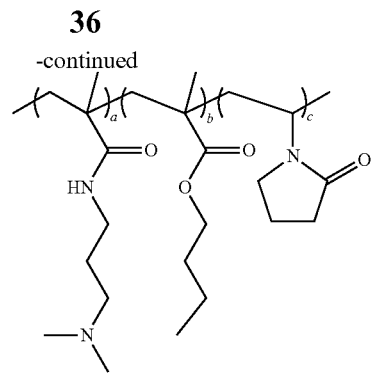

Isopropanol (204.0 g), N-vinyl pyrrolidone (VP) (23.47 g), N-(3-dimethylaminopropyl) methacrylamide (DMAPMA) (1.80 g), and butyl methacrylate (BMA) (1.88 g) were loaded into a glass kettle reactor. The mixture was purged with nitrogen and then heated under nitrogen to 81° C. with stirring at 200 rpm. Meanwhile, a repeating unit premix was prepared with 96.00 g of isopropanol, 7.19 g of DMAPMA, and 7.51 g of BMA. At t=0, 0.14 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.14 g each) and t=4, 6 hour (0.56 g each). After the last initiator addition, the reactor was kept stiffing at 81° C. for 1 hour. The polymer solution was then cooled and discharged.

Example 2

Synthesis of 12% N-(3-Dimethylaminopropyl) Methacrylamide/40% Butyl Methacrylate/48% N-vinyl Pyrrolidone (Molar Ratios) Terpolymer

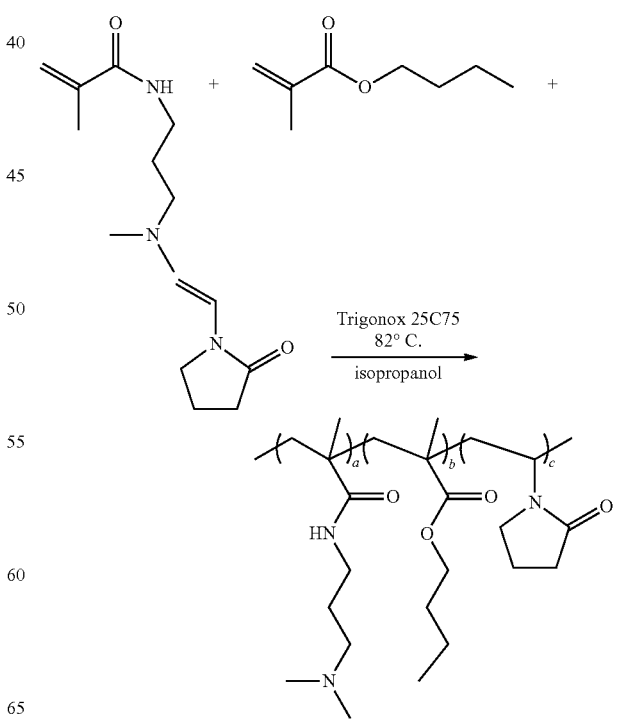

Isopropanol (184.0 g), VP (16.0 g), DMAPMA (1.23 g), and BMA (3.41 g) were loaded into a glass kettle reactor. The mixture was purged with nitrogen and then heated under nitrogen to 82° C. with stiffing at 200 rpm. Meanwhile, a repeating unit premix was prepared with 96.00 g of isopropanol, 4.90 g of DMAPMA, and 13.65 g of BMA. At t=0, 0.13 g of Trigonox® 25C75 (AkzoNobel, t-butyl peroxypivalate initiator) was charged into the reactor. The repeating unit premix was emptied into the reactor at a constant rate in 3 hours. Additional shots of Trigonox® 25C75 were added at t=1, 2, 3 hour (0.13 g each) and t=4, 6 hour (0.53 g each). After the last initiator addition, the reactor was kept stirring at 82° C. for 1 hour. The polymer solution was then cooled and discharged.

Example 3

Synthesis 40% N-(3-Dimethylaminopropyl) Methacrylamide/20% Butyl Methacrylate/of 40% N-vinyl Pyrrolidone (Molar Ratios) Terpolymer

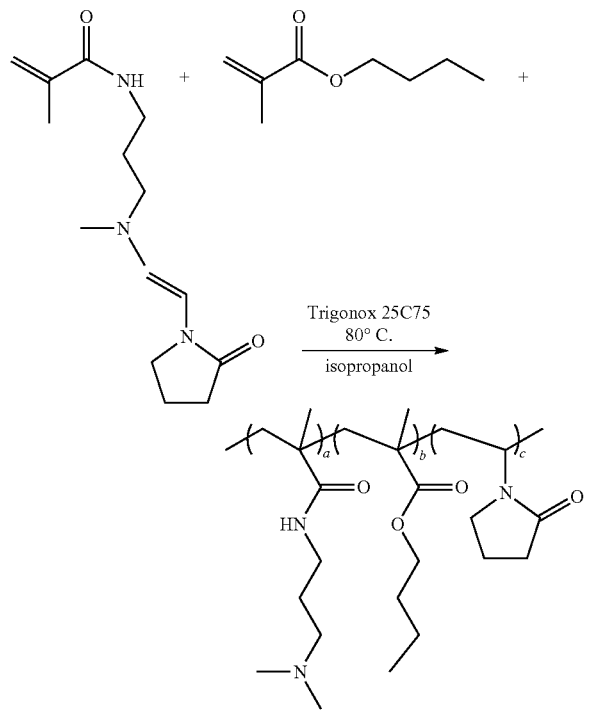

A quantity of 338.00 g of isopropanol, 22.23 g of VP, 6.81 g of DMAPMA, and 2.84 g of BMA were loaded into a glass kettle reactor. The mixture was purged with nitrogen and then heated under nitrogen to 80° C. with stirring at 200 rpm. Meanwhile, a repeating unit premix was prepared with 152.00 g of isopropanol, 27.24 g of DMAPMA, and 11.38 g of BMA. At t=0, 0.25 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.25 g each) and t=4, 6 hour (1.00 g each). After the last initiator addition, the reactor was kept stirring at 80° C. for 1 hour. The polymer solution was then cooled and discharged.

The relative viscosity was measured for a 1% (wt/v) polymer solution in ethanol at 25° C., and found to be 1.13. Part of the polymer solution was then neutralized by 1 M HCl solution (1.1 molar of DMAPMA). The isopropanol was removed by solvent exchange with water. The water was then removed by vacuum stripping and a slightly yellow, fine powder was resulted. The polymer was found to give clear solutions in water for concentration at least up to and including 10% by weight.

Example 4

Synthesis of 30% N-(3-Dimethylaminopropyl) Methacrylamide/40% Butyl Methacrylate/30% N-vinyl Pyrrolidone (Molar Ratios) Terpolymer

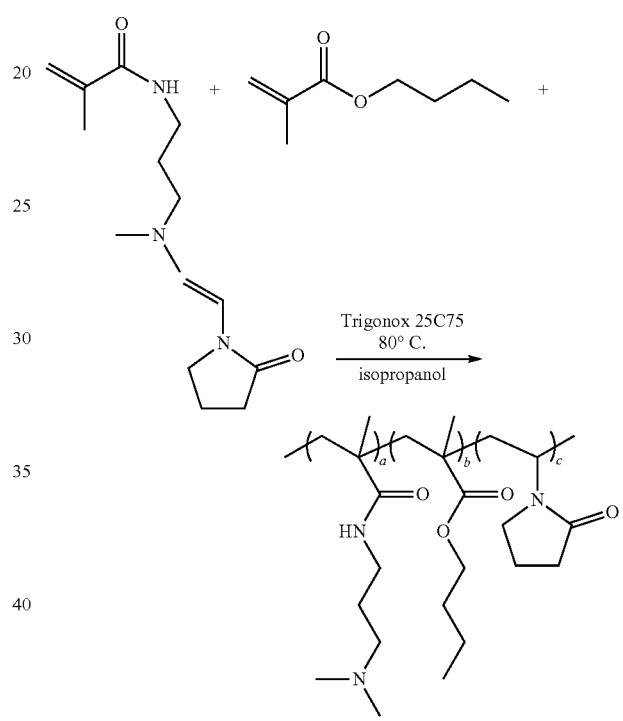

A quantity of 338.00 g of isopropanol, 16.67 g of VP, 5.11 g of DMAPMA, and 5.69 g of BMA were loaded into a glass kettle reactor. The mixture was purged with nitrogen and then heated under nitrogen to 80° C. with stirring at 200 rpm. Meanwhile, a repeating unit premix was prepared with 152.00 g of isopropanol, 20.43 g of DMAPMA, and 22.75 g of BMA. At t=0, 0.25 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.25 g each) and t=4, 6 hour (1.00 g each). After the last initiator addition, the reactor was kept stirring at 80° C. for 1 hour. The polymer solution was then cooled and discharged.

The relative viscosity was measured for a 1% (wt/v) polymer solution in ethanol at 25° C., and found to be 1.12. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted. The polymer was found to give clear solutions in water for concentration at least up to and including 5% by weight. A 10% (w/w) solution in water sometimes was slightly hazy.

Example 5

Synthesis of 64% N-(3-Dimethylaminopropyl) Methacrylamide/20% Butyl Methacrylate/16% N-vinyl Pyrrolidone (Molar Ratios) Terpolymer

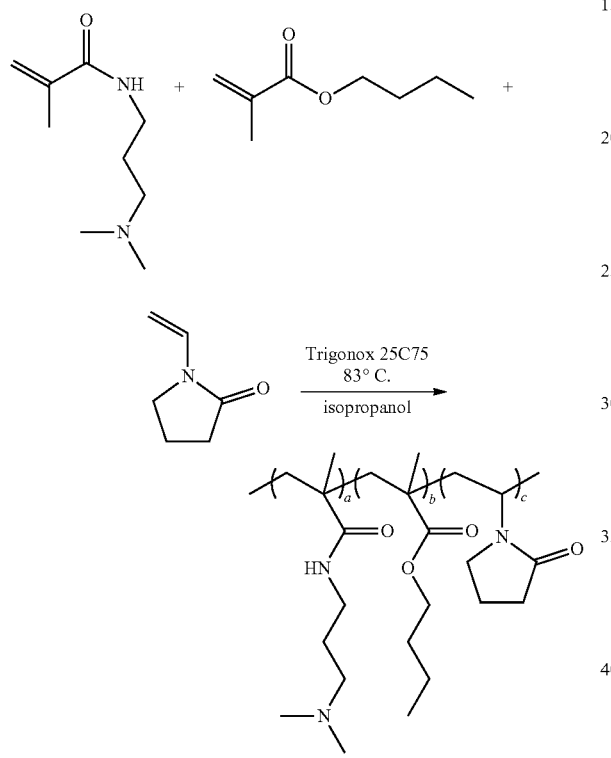

A quantity of 338.00 g of isopropanol, 8.89 g of VP, 10.90 g of DMAPMA, and 2.84 g of BMA were loaded into a glass kettle reactor. The mixture was purged with nitrogen and then heated under nitrogen to 83° C. with stirring at 200 rpm. Meanwhile, a repeating unit premix was prepared with 152.00 g of isopropanol, 43.58 g of DMAPMA, and 11.38 g of BMA. At t=0, 0.25 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.25 g each) and t=4, 6 hour (1.00 g each). After the last initiator addition, the reactor was kept stirring at 83° C. for 1 hour. The polymer solution was then cooled and discharged.

The relative viscosity was measured for a 1% (wt/v) polymer solution in ethanol at 25° C., and found to be 1.10. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Example 6

Synthesis of 48% N-(3-Dimethylaminopropyl) Methacrylamide/40% Butyl Methacrylate/12% N-vinyl Pyrrolidone (Molar Ratios) Terpolymer

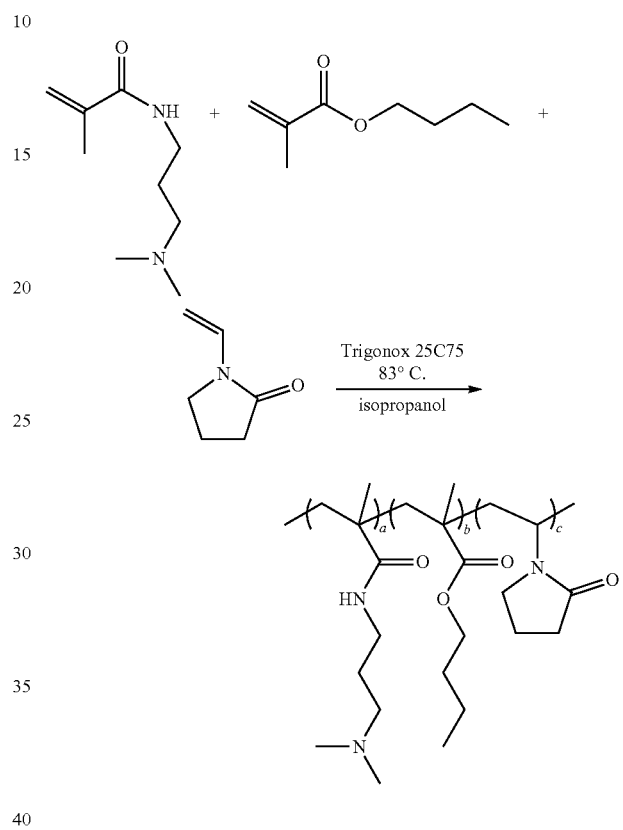

A quantity of 338.00 g of isopropanol, 6.67 g of VP, 8.17 g of DMAPMA, and 5.69 g of BMA were loaded into a glass kettle reactor. The mixture was purged with nitrogen and then heated under nitrogen to 83° C. with stirring at 200 rpm. Meanwhile, a repeating unit premix was prepared with 152.00 g of isopropanol, 32.69 g of DMAPMA, and 22.75 g of BMA. At t=0, 0.25 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.25 g each) and t=4, 6 hour (1.00 g each). After the last initiator addition, the reactor was kept stirring at 83° C. for 1 hour. The polymer solution was then cooled and discharged.

The relative viscosity was measured for a 1% (wt/v) polymer solution in ethanol at 25° C., and found to be 1.10. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Molecular weights were measured as a 0.15% polymer solution in methanol/water mobile phase in using PEO/PEG standards. $M_w$ was found to be 2,640 Da, and $M_n$ was determined to be 1,170 Da.

Example 7

Synthesis of 30% N-(3-Dimethylaminopropyl) Methacrylamide/40% Butyl Methacrylate/30% N-vinyl Pyrrolidone (Molar Ratios) Terpolymer

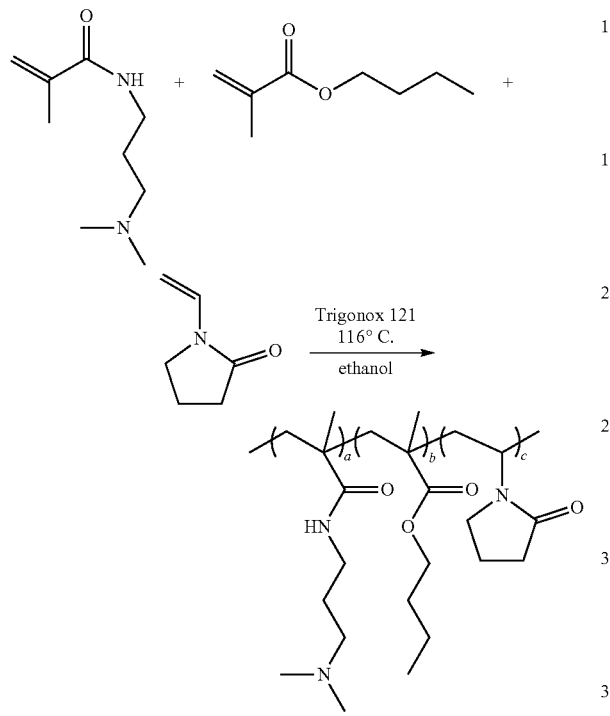

A quantity of 30.00 g of ethanol, 33.34 g of VP, 10.22 g of DMAPMA, and 11.38 g of BMA were loaded into an Autoclave Engineers' reactor. The mixture was purged with nitrogen and then heated under nitrogen to 116° C. with stiffing at 200 rpm. Meanwhile, a pump was filled with a mixture of 64.00 g of ethanol, 40.86 g of DMAPMA, and 45.50 g of BMA. At t=0, 0.58 g of Trigonox® 121 (AkzoNobel, t-amyl peroxy-2-ethylhexanoate initiator) was charged into the reactor. Then the contents of the pump were emptied into the reactor at a constant rate over the next 3 hours. Additional 12 shots of Trigonox® 121 were added into the reactor every 15 min (0.58 g each). Then the reaction was cooled to 92° C. Starting at t=4 hour, 6 shots of Trigonox® 121 were added into the reactor every hour (1.17 g each). After the last initiator addition, the reactor was kept stiffing at 92° C. for 3 hours. The polymer solution was then cooled and discharged.

The relative viscosity was measured for a 1% (wt/v) polymer solution in ethanol at 25° C., and found to be 1.11. Part of the polymer solution was then neutralized by 1 M HCl solution (1:1 molar of DMAPMA). The ethanol was removed by solvent exchange with water. The water was then removed by vacuum stripping and a slightly yellow, fine powder was resulted.

Molecular weights were measured as a 0.15% polymer solution in methanol/water mobile phase in using PEO/PEG standards. $M_w$ was found to be 5,000 Da, and $M_n$ was determined to be 826 Da.

Example 8

Synthesis of 30% N-(3-Dimethylaminopropyl) Methacrylamide/40% Butyl Methacrylate/30% N-vinyl Pyrrolidone (Molar Ratios) Terpolymer

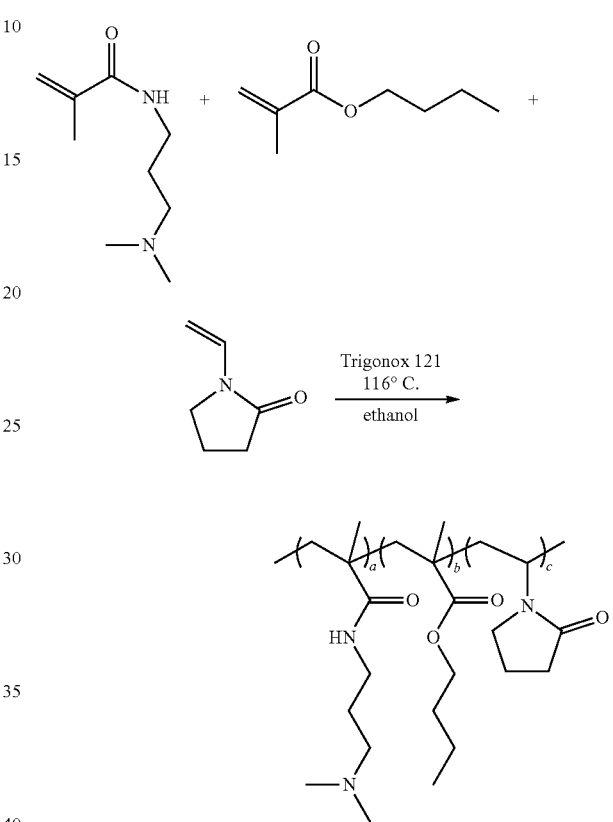

A quantity of 130.00 g of ethanol, 33.34 g of VP, 25.54 g of DMAPMA, and 11.38 g of BMA were loaded into an Autoclave Engineers' reactor. The mixture was purged with nitrogen and then heated to 116° C. under nitrogen with stiffing at 200 rpm. Meanwhile, a pump was filled with a mixture of 64.00 g of ethanol, 25.54 g of DMAPMA, and 45.50 g of BMA. At t=0, 0.58 g of Trigonox® 121 (AkzoNobel, t-amyl peroxy-2-ethylhexanoate initiator) was charged into the reactor. Then the contents of the pump were emptied into the reactor at a constant rate over the next 3 hours. Additional 12 shots of Trigonox® 121 were added into the reactor every 15 min (0.58 g each). Then the reaction was cooled to 92° C. Starting at t=4 hour, 5 shots of Trigonox® 121 were added into the reactor every hour (1.17 g each for the first 4 shots and 2.33 g for the last shot). After the last initiator addition, the reactor was kept stirring at 92° C. for 3 hours. The polymer solution was then cooled and discharged. Part of the polymer solution was then neutralized by 1 M HCl solution (1:1 molar of DMAPMA). The ethanol was removed by solvent exchange with water. The water was then removed by vacuum stripping and a slightly yellow, fine powder was resulted.

Molecular weights were measured as a 0.15% polymer solution in methanol/water mobile phase in using PEO/PEG standards. $M_w$ was found to be 8,250 Da, and $M_n$ was determined to be 1,180 Da.

Example 9

Synthesis of 30% N-(3-Dimethylaminopropyl) Methacrylamide/40% Butyl Methacrylate/30% N-vinyl Pyrrolidone (Molar Ratios) Terpolymer

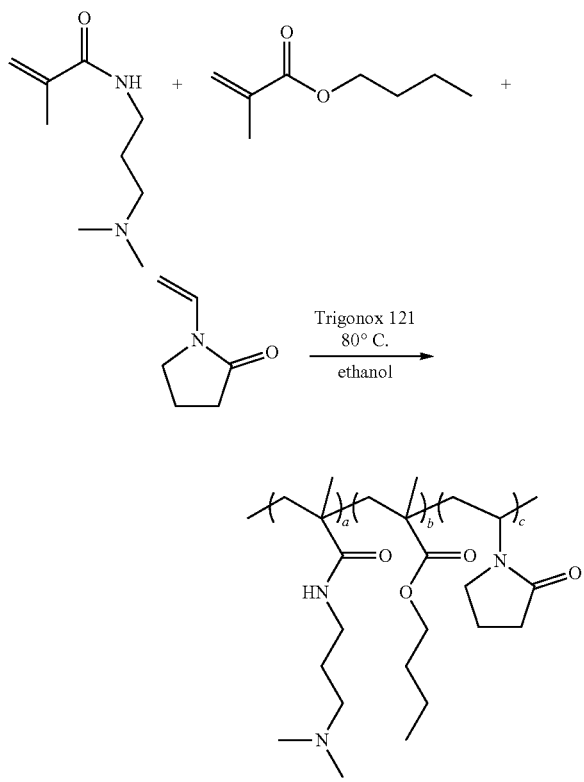

A quantity of 200.00 g of ethanol, 33.34 g of VP, 10.22 g of DMAPMA, and 11.38 g of BMA were loaded into a glass kettle reactor. The mixture was purged with nitrogen and then heated to 80° C. under nitrogen with stirring at 200 rpm. Meanwhile, a repeating unit premix was prepared with 40.86 g of DMAPMA and 45.50 g of BMA. Starting at t=0, 1.70 g of Trigonox® 121 (AkzoNobel, t-amyl peroxy-2-ethyl-hexanoate initiator) was charged into the reactor in 3 hours and the contents of the repeating unit premix were also emptied into the reactor at a constant rate over the 3 hours. Starting at t=5 hour, additional 2.85 g of Trigonox® 121 was added into the reactor over 2 hours. Then the reactor was kept stirring at 80° C. for 1 hour. The polymer solution was then cooled and discharged.

The relative viscosity was measured for a 1% (wt/v) polymer solution in ethanol at 25° C., and found to be 1.29.

Example 10

Synthesis of 30% N-(3-Dimethylaminopropyl) Methacrylamide/40% Butyl Methacrylate/30% N-vinyl Pyrrolidone (Molar Ratios) Terpolymer

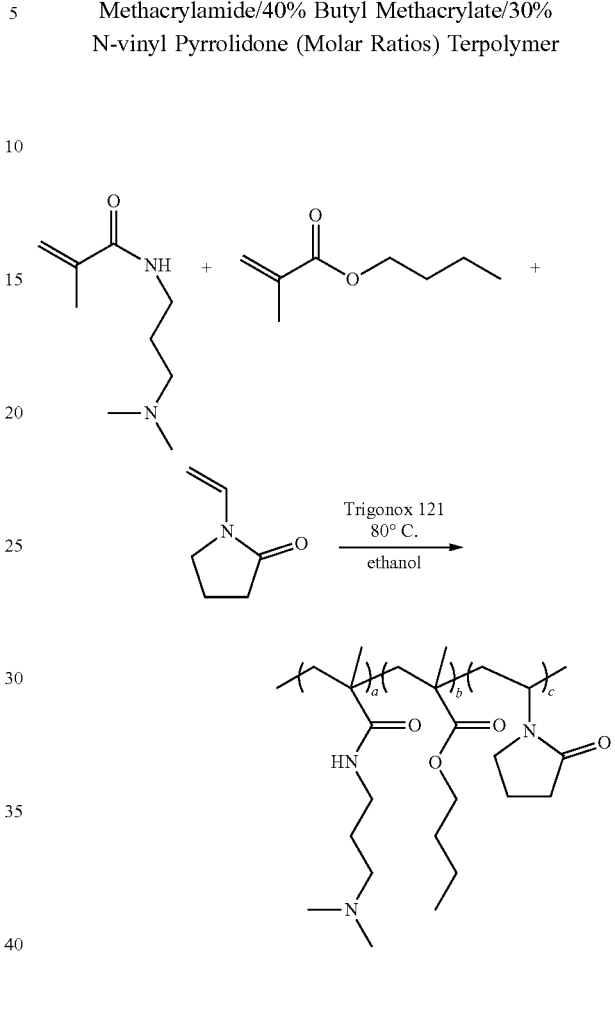

A quantity of 85.00 g of ethanol, 33.34 g of VP, 10.22 g of DMAPMA, and 11.38 g of BMA were loaded into a glass kettle reactor. The mixture was purged with nitrogen and then heated to 80° C. under nitrogen with stirring at 200 rpm. Meanwhile, a repeating unit premix was prepared with 40.86 g of DMAPMA and 45.50 g of BMA. Starting at t=0, 0.85 g of Trigonox® 121 (AkzoNobel, t-amyl peroxy-2-ethyl-hexanoate initiator) was charged into the reactor in 3 hours and the contents of the repeating unit premix were also emptied into the reactor at a constant rate over the 3 hours. Starting at t=5 hour, additional 2.85 g of Trigonox® 121 was added into the reactor over 2 hours. Then the reactor was kept stirring at 80° C. for 1 hour. The polymer solution was then cooled and discharged.

Molecular weights were measured as a 0.15% polymer solution in methanol/water mobile phase in using PEO/PEG standards. $M_w$ was found to be 21,400 Da, and $M_n$ was determined to be 5,220 Da.

The relative viscosity was measured for a 1% (wt/v) polymer solution in ethanol at 25° C., and found to be 1.97.

Example 11

Synthesis of 30% N-(3-Dimethylaminopropyl) Methacrylamide/40% 2-Ethylhexyl Methacrylate/30% N-vinyl Pyrrolidone (Molar Ratios) Terpolymer

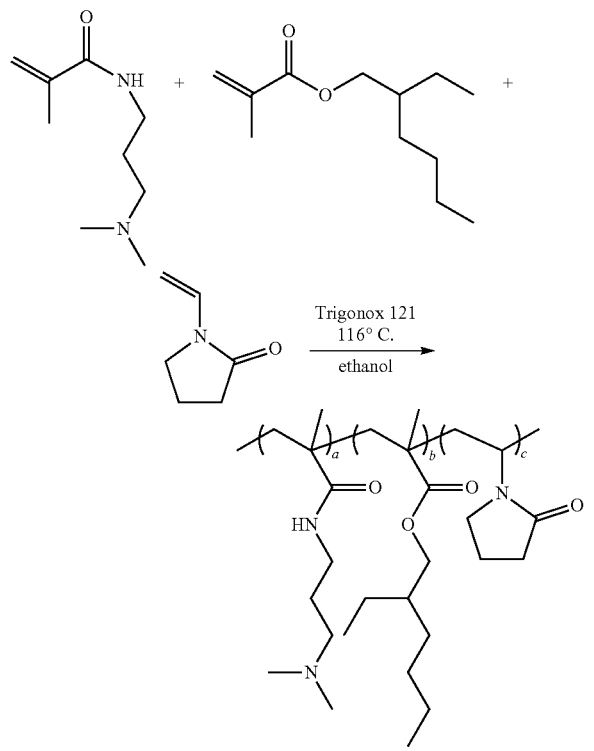

A quantity of 130.00 g of ethanol, 28.34 g of VP, 21.71 g of DMAPMA, and 13.48 g of 2-ethylhexyl methacrylate (EHMA) were loaded into an Autoclave Engineers' reactor. The mixture was purged with nitrogen and then heated to 116° C. under nitrogen with stirring at 200 rpm. Meanwhile, a pump was filled with a mixture of 64.00 g of ethanol, 21.71 g of DMAPMA, and 53.94 g of EHMA. At t=0, 0.57 g of Trigonox® 121 (AkzoNobel, t-amyl peroxy-2-ethylhexanoate initiator) was charged into the reactor. Then the contents of the pump were emptied into the reactor at a constant rate over the next 3 hours. Additional Trigonox® 121 was charged into the reactor over 2.75 hours (6.83 g). Then the reaction was cooled to 91° C. Starting at t=4 hour, 4 shots of Trigonox® 121 were added into the reactor every hour (1.75 g each). After the last initiator addition, the reactor was kept stirring at 91° C. for 3 hours. The polymer solution was then cooled and discharged.

The relative viscosity was measured for a 1% (wt/v) polymer solution in ethanol at 25° C., and found to be 1.10. Part of the polymer solution was then neutralized by 1 M HCl solution (1:1 molar of DMAPMA). The ethanol was removed by solvent exchange with water. The water was then removed by vacuum stripping and a slightly yellow, fine powder was resulted. The polymer was found to give a hazy solution at 1% weight addition in water. Cloudy solutions were produced in water for solutions containing 2.5% to 10% (w/w) polymer.

Molecular weights were measured as a 0.15% polymer solution in methanol/water mobile phase in using PEO/PEG standards. $M_w$ was found to be 2,280 Da, and $M_n$ was determined to be 686 Da.

Example 12

Synthesis of 40% N-(3-Dimethylaminopropyl) Methacrylamide/20% 2-Ethylhexyl Methacrylate/40% N-vinyl Pyrrolidone (Molar Ratios) Terpolymer

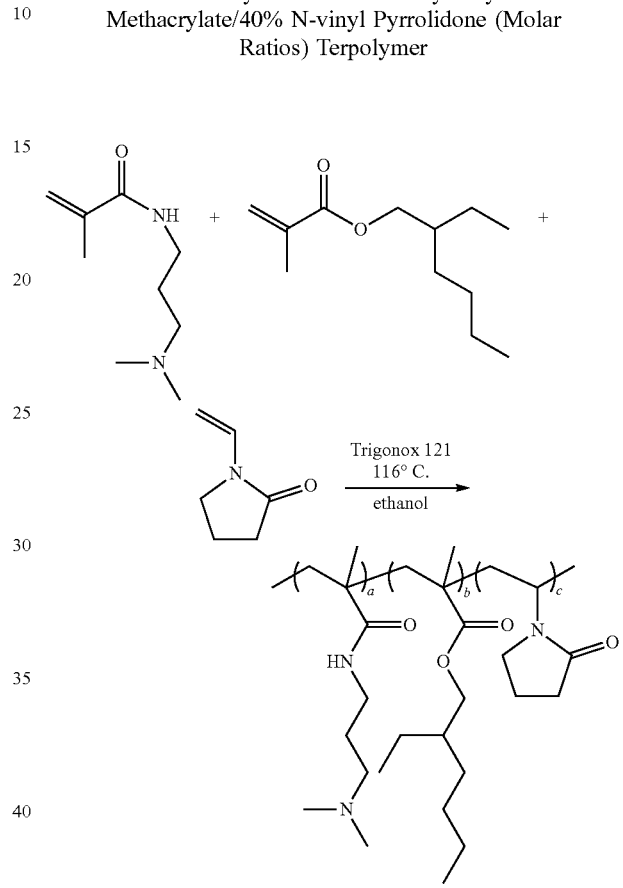

A quantity of 130.00 g of ethanol, 37.79 g of VP, 28.94 g of DMAPMA, and 6.74 g of EHMA were loaded into an Autoclave Engineers' reactor. The mixture was purged with nitrogen and then heated to 116° C. under nitrogen with stirring at 200 rpm. Meanwhile, a pump was filled with a mixture of 45.00 g of ethanol, 28.94 g of DMAPMA, and 26.98 g of EHMA. Starting at t=0, 6.90 g of Trigonox® 121 (AkzoNobel, t-amyl peroxy-2-ethylhexanoate initiator) was charged into the reactor over 3 hours. The contents of the pump were also emptied into the reactor at a constant rate in 3 hours. Then the reaction was cooled to 91° C. Starting at t=4 hour, 5 shots of Trigonox® 121 were added into the reactor every hour (1.30 g each). After the last initiator addition, the reactor was kept stirring at 91° C. for 3 hours. The polymer solution was then cooled and discharged. The relative viscosity was measured for a 1% (wt/v) polymer solution in ethanol at 25° C., and found to be 1.20. Part of the polymer solution was then neutralized by 1 M HCl solution (1:1 molar of DMAPMA). The ethanol was removed by solvent exchange with water. The water was then removed by vacuum stripping and a slightly yellow, fine powder was resulted.

Molecular weights were measured as a 0.15% polymer solution in methanol/water mobile phase in using PEO/PEG standards. $M_w$ was found to be 13,100 Da, and $M_n$ was determined to be 1,250 Da.

Example 13

Synthesis of 16% N-(3-Dimethylaminopropyl) Methacrylamide/20% Lauryl Methacrylate/64% N-vinyl Pyrrolidone (Molar Ratios) Terpolymer

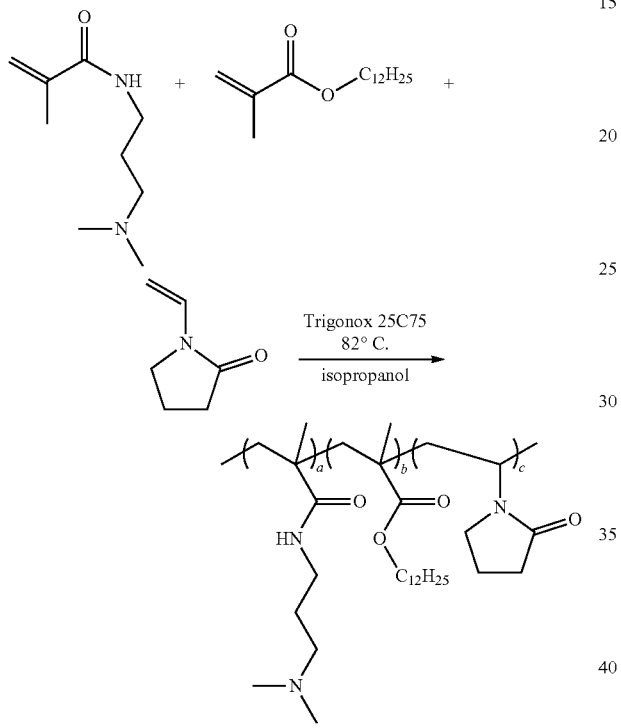

A quantity of 159.00 g of isopropanol, 17.78 g of VP, 1.36 g of DMAPMA, and 2.54 g of lauryl methacrylate (LMA) were loaded into a glass kettle reactor. The mixture was purged with nitrogen and then heated to 82° C. under nitrogen with stirring at 200 rpm. Meanwhile, a repeating unit premix was prepared with 36.00 g of isopropanol, 5.45 g of DMAPMA, and 10.18 g of LMA. At t=0, 0.125 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 was added at t=1, 2, 3 hour (0.125 g each) and t=4, 5, 6, 7 hour (0.25 g each). After the last initiator addition, the reactor was kept stirring at 82° C. for 1 hour. The polymer solution was then cooled and discharged.

The relative viscosity was measured for a 1% (wt/v) polymer solution in ethanol at 25° C., and found to be 1.13. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Example 14

Synthesis of 12% N-(3-Dimethylaminopropyl) Methacrylamide/40% Lauryl Methacrylate/48% N-vinyl Pyrrolidone (Molar Ratios) Terpolymer

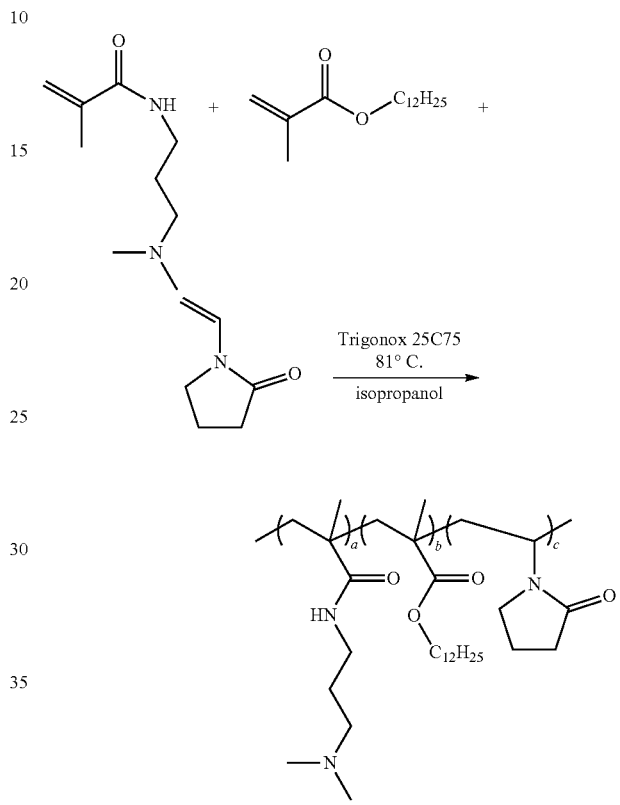

A quantity of 170.00 g of isopropanol, 13.34 g of VP, 1.02 g of DMAPMA, and 5.09 g of LMA were loaded into a glass kettle reactor. The mixture was purged with nitrogen and then heated to 81° C. under nitrogen with stirring at 200 rpm. Meanwhile, a repeating unit premix was prepared with 80.00 g of isopropanol, 4.09 g of DMAPMA, and 20.36 g of LMA. At t=0, 0.125 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.125 g each) and t=4, 5, 6, 7 hour (0.25 g each). After the last initiator addition, the reactor was kept stirring at 81° C. for 1 hour. The polymer solution was then cooled and discharged.

The relative viscosity was measured for a 1% (wt/v) polymer solution in ethanol at 25° C., and found to be 1.12. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Example 15

Synthesis of 40% N-(3-Dimethylaminopropyl) Methacrylamide/20% Lauryl Methacrylate/40% N-vinyl Pyrrolidone (Molar Ratios) Terpolymer

Example 16

Synthesis of 30% N-(3-Dimethylaminopropyl) Methacrylamide/40% Lauryl Methacrylate/30% N-vinyl Pyrrolidone (Molar Ratios) Terpolymer

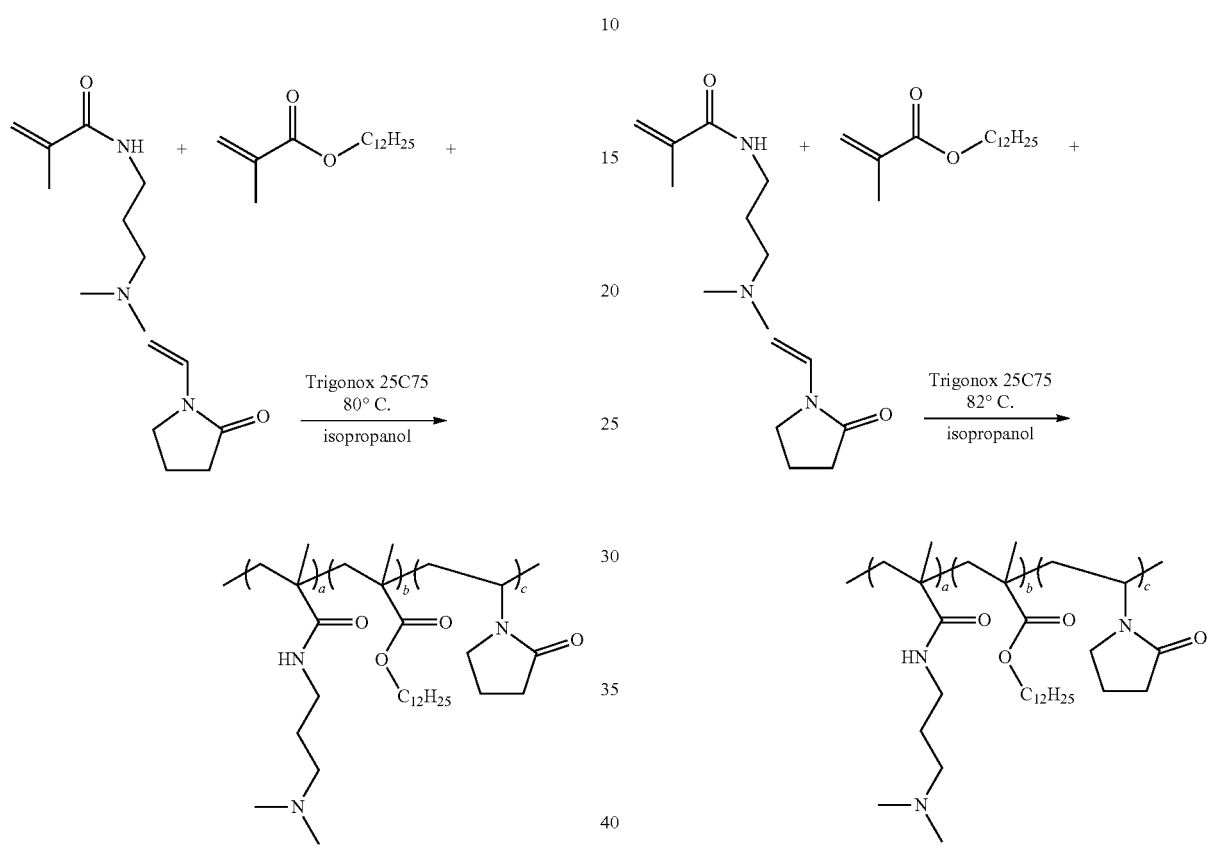

A quantity of 165.00 g of isopropanol, 11.11 g of VP, 3.41 g of DMAPMA, and 2.54 g of LMA were loaded into a glass kettle reactor. The mixture was purged with nitrogen and then heated to 80° C. under nitrogen with stirring at 200 rpm. Meanwhile, a repeating unit premix was prepared with 60.00 g of isopropanol, 13.62 g of DMAPMA, and 10.18 g of LMA. At t=0, 0.125 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.125 g each) and t=4, 5, 6, 7 hour (0.25 g each). After the last initiator addition, the reactor was kept stirring at 80° C. for 1 hour. The polymer solution was then cooled and discharged.

The relative viscosity was measured for a 1% (wt/v) polymer solution in ethanol at 25° C., and found to be 1.12. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

A quantity of 199.00 g of isopropanol, 8.34 g of VP, 2.55 g of DMAPMA, and 5.09 g of LMA were loaded into a glass kettle reactor. The mixture was purged with nitrogen and then heated to 82° C. under nitrogen with stirring at 200 rpm. Meanwhile, a repeating unit premix was prepared with 76.00 g of isopropanol, 10.22 g of DMAPMA, and 20.35 g of LMA. At t=0, 0.125 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.125 g each) and t=4, 5, 6, 7 hour (0.25 g each). After the last initiator addition, the reactor was kept stirring at 82° C. for 1 hour. The polymer solution was then cooled and discharged.

The relative viscosity was measured for a 1% (wt/v) polymer solution in ethanol at 25° C., and found to be 1.11. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Example 17

Synthesis of 64% N-(3-Dimethylaminopropyl) Methacrylamide/20% Lauryl Methacrylate/16% N-vinyl Pyrrolidone (Molar Ratios) Terpolymer

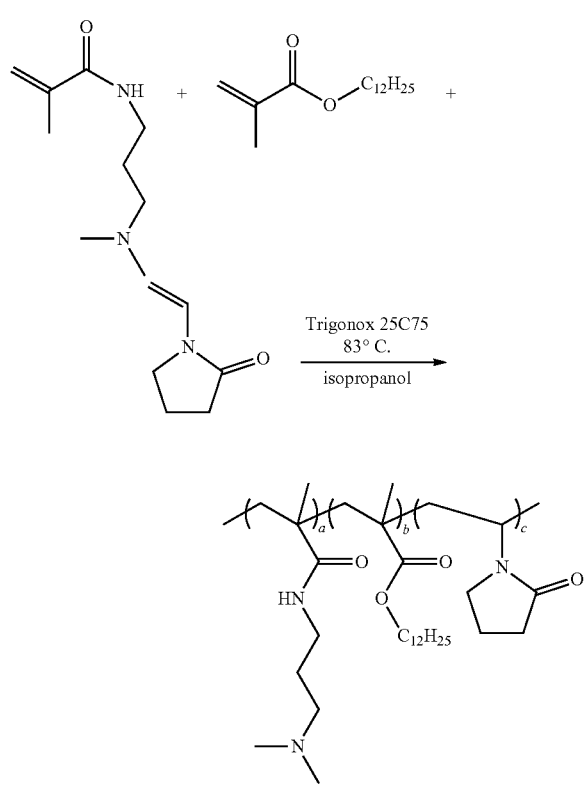

A quantity of 130.00 g of isopropanol, 4.45 g of VP, 5.45 g of DMAPMA, and 2.54 g of LMA were loaded into a glass kettle reactor. The mixture was purged with nitrogen and then heated to 83° C. under nitrogen with stirring at 200 rpm. Meanwhile, a repeating unit premix was prepared with 120.00 g of isopropanol, 21.79 g of DMAPMA, and 10.18 g of LMA. At t=0, 0.125 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.125 g each) and t=4, 5, 6, 7 hour (0.25 g each). After the last initiator addition, the reactor was kept stirring at 83° C. for 1 hour. The polymer solution was then cooled and discharged The relative viscosity was measured for a 1% (wt/v) polymer solution in ethanol at 25° C., and found to be 1.13. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Example 18

Synthesis of 48% N-(3-Dimethylaminopropyl) Methacrylamide/40% Lauryl Methacrylate/12% N-vinyl Pyrrolidone (Molar Ratios) Terpolymer

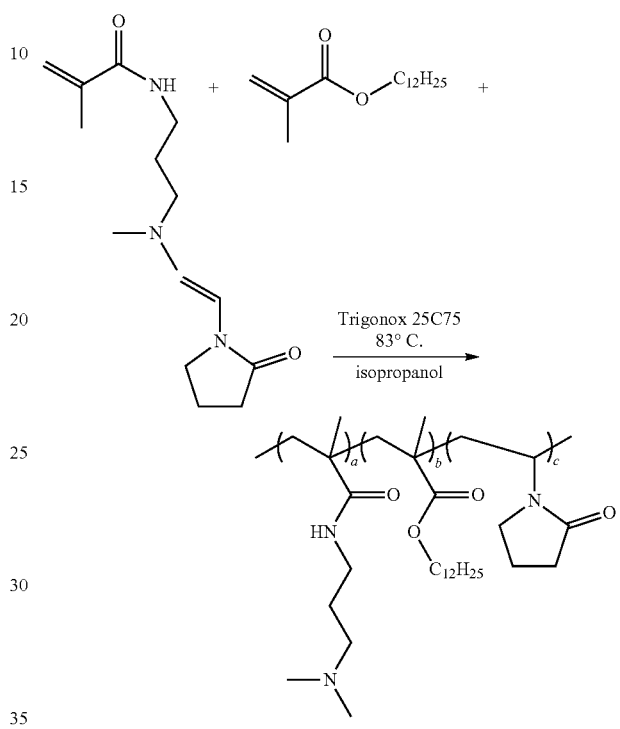

A quantity of 140.00 g of isopropanol, 3.33 g of VP, 4.09 g of DMAPMA, and 5.09 g of LMA were loaded into a glass kettle reactor. The mixture was purged with nitrogen and then heated to 83° C. under nitrogen with stirring at 200 rpm. Meanwhile, a repeating unit premix was prepared with 160.00 g of isopropanol, 16.34 g of DMAPMA, and 20.35 g of LMA. At t=0, 0.125 g of Trigonox® 25C75 (AkzoNobel, t-butyl peroxy-pivalate initiator) was charged into the reactor. The repeating unit premix was emptied into the reactor at a constant rate in 3 hours. Additional shots of Trigonox® 25C75 were added at t=1, 2, 3 hour (0.125 g each) and t=4, 5, 6, 7 hour (0.25 g each). After the last initiator addition, the reactor was kept stirring at 83° C. for 1 hour. The polymer solution was then cooled and discharged.

The relative viscosity was measured for a 1% (wt/v) polymer solution in ethanol at 25° C., and found to be 1.09. Part of the polymer solution was then neutralized by 1 M HCl solution (1:1 molar of DMAPMA). The isopropanol was removed by solvent exchange with water. The water was then removed by vacuum stripping and a slightly yellow, fine powder was resulted.

Comparative Example 1

Antimicrobial Activity of Repeating Units Via Streak Plate Method

The antimicrobial activity of N-vinyl-2-pyrrolidone (VP), dimethylaminopropyl methacrylamide (DMAPMA), and butyl methacrylate (BMA) were evaluated using a streak plate method. Briefly, stock solution of each microorganism was prepared by growing the bacterial cells in tryptic soy broth (TSB) or the fungi cells in yeast malt broth (YM) to reach a concentration of about $10^8$-$10^9$ cfu/mL. Molten agar (TSA or YM) was seeded with each microorganism to obtain a microbial concentration of about $10^5$-$10^6$ cfu/mL. Plates were allowed to solidify. Monomer plates were challenged with the following microbes: *Staphylococcus aureus* (ATCC 6538), *Escherichia coli* (ATCC 8730), *Pseudomonas aeruginosa* (ATCC 9027), *Candida albicans* (ATCC 10231) and *Aspergillus niger* (ATCC 16404). The repeating units were tested as a 1% solution in water, and DMAPMA solution was adjusted to pH 6-7 prior to testing. The plates were refrigerated for 24 hours to allow for the polymer to diffuse and were then placed in the incubator (32° C. for bacteria plates, 28° C. for fungal plates) for 24-72 hrs. Growth inhibition along the polymeric streak or polymer sprinkles was considered as indicative of antimicrobial activity. Seeded plates without polymers were used as positive controls for microbial growth.

No repeating unit showed antimicrobial activity for the microbes tested.

Example 19

Antimicrobial Testing Via Plate Streak Method

The antimicrobial activity of the various polymers was evaluated using a plate streak method. The method of the Comparative Example was followed, except polymers were tested either as a 5% solution in water or as powders by streaking the solution or sprinkling the polymers over the microbial seeded plate, respectively. The results of the streak test for various polymers are summarized in the Table 1 below. A "−" symbol indicates that antimicrobial activity was observed (growth inhibition) whereas a "+" symbol indicates that no antimicrobial activity was detected in this assay.

TABLE 1

Microbial test results of Example 19

| polymer | growth inhibition | | | | |
|---|---|---|---|---|---|
| | S. aureus | E. coli | P. aeruginosa | A. niger | C. albicans |
| Example 3 | − | − | − | + | + |
| Example 4 | − | − | − | + | + |
| Example 5 | − | − | − | + | + |
| Example 6 | − | − | − | + | + |
| Example 7 | − | + | + | + | + |
| Example 8 | − | − | − | + | + |
| Example 11 | − | − | + | + | + |
| Example 12 | − | + | + | − | − |
| Example 13 | + | + | + | + | + |
| Example 14 | + | + | + | + | + |
| Example 15 | − | + | + | + | + |
| Example 16 | − | + | + | + | + |
| Example 17 | − | + | + | + | + |
| Example 18 | − | + | + | + | + |

As shown in the Table 1 above, multifunctional polymers embraced by the invention showed antimicrobial activity.

Example 20

The antimicrobial activity of selected polymers was further evaluated by a shake flask method. Briefly, 2% by wt. of the polymers were added to TSB. The pH of the media was adjusted to a pH of about 6. Each flask was then inoculated with a microorganism to achieve an initial concentration of about $10^6$ cfu/mL and incubated with shaking at 32° C. Microbial counts were conducted after 48 hours by serially diluting and plating onto TSA media. The log reduction values (Log CFU/mL control at t=48 h–Log CFU/mL treated sample at t=48 hours) of the polymer in Example 8 tested against *S. aureus, E. coli* and *P. aeruginosa* were >7.2, >7.2, and 6.0, respectively. Therefore, the antimicrobial activity of Example 8 polymer when tested at 2% resulted in total growth inhibition of both *S. aureus* and *E. coli*.

Example 21

Compatibility with Formulation Polymers

The poly(DMAPMA/BMA/VP) multifunctional polymer of Examples 8 was evaluated for compatibility with four formulation polymers: polyquaternium-69 (Aquastyle™ 300AF, Ashland Specialty Ingredients), polyimide-1 (Aquaflex™ XL30, Ashland Specialty Ingredients), and polyquaternium-55 (Styleze™ W20, Ashland Specialty Ingredients). To evaluate compatibility a total of twenty-five 10 gram samples consisting of a ranging amount of candidate polymer, existing product and water were prepared. Then, 1-5% of the candidate polymer (based on 10 g total sample) was mixed with 1-5% of existing product (based on 10 g total sample) and water was added to bring total mass of sample to ten grams. Amount of all constituent components were adjusted to reflect percent solids.

Overall, the polymer showed good compatibility with the formulation polymers (Tables 2). In the case of polyquaternium-69 and polyimide-1, clear solutions existed at virtually all evaluated levels, with only slight haze at the highest concentrations, were observed (Tables 2). With polyquaternium-55 clear solutions were observed until 2-3% of the multifunctional polymer and existing product (Table 2).

TABLE 2

Compatibility of 30% VP/30% DMAPMA/40% BMA (molar ratios) with formulation polymers.

| formulation polymer | multifunctional polymer addition level (w/w) | | | | | pH |
|---|---|---|---|---|---|---|
| | 1% | 2% | 3% | 4% | 5% | |
| polyquaternium-69 | | | | | | |
| 1% | clear | clear | clear | clear | clear | 5-6 |
| 2% | clear | clear | clear | clear | clear | |
| 3% | clear | clear | clear | clear | clear | |
| 4% | clear | clear | clear | clear | clear | |
| 5% | clear | clear | clear | clear | clear | |
| polyimide-1 | | | | | | |
| 1% | clear | clear | clear | clear | clear | 6.5-7.5 |
| 2% | clear | clear | clear | clear | clear | |
| 3% | clear | clear | clear | clear | clear | |
| 4% | clear | clear | clear | clear | slightly hazy | |
| 5% | clear | clear | clear | clear | slightly hazy | |

TABLE 2-continued

Compatibility of 30% VP/30% DMAPMA/40% BMA (molar ratios) with formulation polymers.

| formulation polymer | multifunctional polymer addition level (w/w) | | | | | pH |
|---|---|---|---|---|---|---|
| | 1% | 2% | 3% | 4% | 5% | |
| polyquaternium-55 | | | | | | |
| 1% | clear | clear | clear | clear | clear | 4.5-5.0 |
| 2% | clear | clear | clear | clear | slightly hazy | |
| 3% | clear | clear | slightly hazy | slightly hazy | hazy | |
| 4% | clear | clear | slightly hazy | slightly hazy | hazy | |
| 5% | clear | clear | slightly hazy | slightly hazy | hazy | |

While a number of embodiments of this invention have been represented, it was apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A terpolymer synthesized from: (A) a first repeating unit A, (B) a second repeating unit B comprising a hydrophobic moiety, and (C) a third repeating unit C, and
wherein:
the weight-average molecular weight of the terpolymer is less than 10,000 Da; and
the terpolymer is selected from the group consisting of:

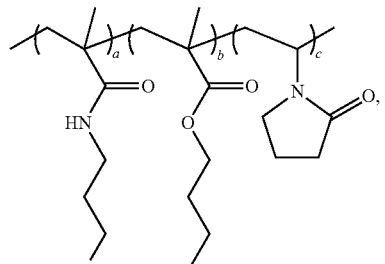

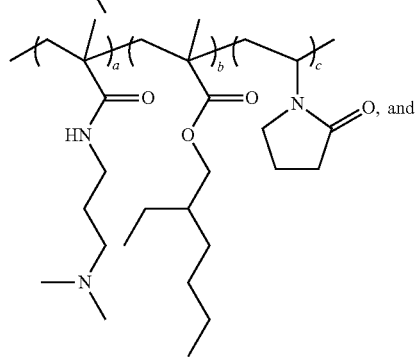

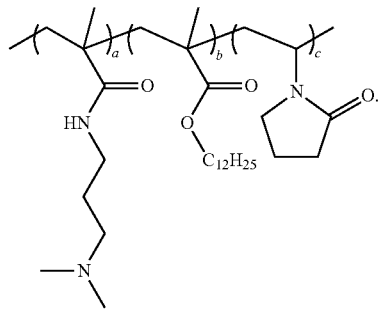

2. The terpolymer according to claim 1 wherein the terpolymer is synthesized by radical polymerization.

3. The terpolymer according to claim 1 wherein a ranges from about 5% to about 80%, b ranges from about 5% to about 60%, and c ranges from about 5% to about 80% (all molar ratios).

4. The terpolymer according to claim 1, wherein the terpolymer exhibits antimicrobial activity against a microbe selected from the group consisting of *S. aureus, E. coli, P. aeruginosa, A. niger, C. albicans*, and mixtures thereof.

5. A composition comprising a terpolymer synthesized from: (A) a first repeating unit A, (B) a second repeating unit B comprising at least one hydrophobic moiety, and (C) a third repeating unit C, and
wherein:
the weight-average molecular weight of the terpolymer is less than 10,000 Da: and
the terpolymer is selected from the group consisting of:

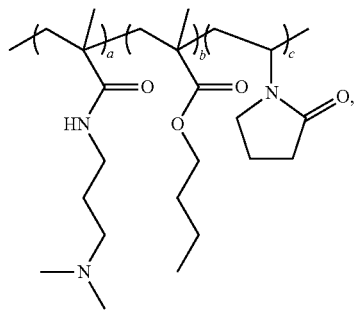

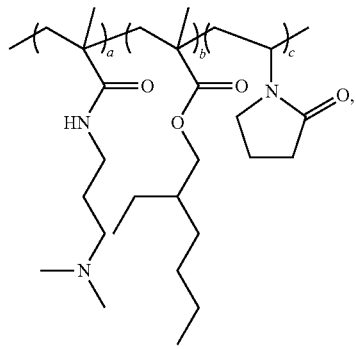

-continued

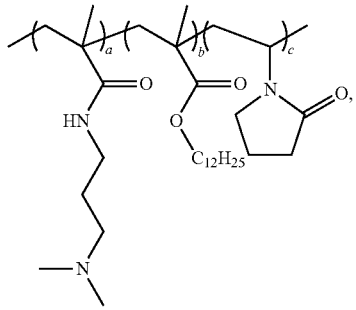

and combinations thereof.

6. The composition according to claim 5 that is a nutrition, food, beverage, pharmaceutical, cleaning, coating, paint, biocide, construction, energy, industrial, oilfield, personal care, household, performance, agricultural, pesticide, veterinary, fuel, lubricant, adhesive, electronic, textile, ink, or membrane composition.

7. The composition according to claim 6, wherein the personal care composition is a skin lotion, skin creme, skin ointment, skin salve, anti-aging creme, moisturizer, deodorant, tanning agent, sun block, sunscreen, foundation, concealer, eyebrow pencil, eye shadow, eye liner, mascara, rouge, finishing powder, lipstick, lip gloss, nail polish, make-up remover, nail polish remover, shampoo, rinse-off conditioner, leave-on conditioner, hair styling gel, hair mousse, hair spray, styling aide, hair color, or hair color remover.

8. The composition according to claim 5, wherein the terpolymer exhibits antimicrobial activity against a microbe selected from the group consisting of *S. aureus, E. coli, P. aeruginosa, A. niger, C. albicans*, and mixtures thereof.

9. A method of providing antimicrobial activity, the method comprising the step: contacting a composition with at least one terpolymer comprising: (A) a first repeating unit A, (B) a second repeating unit B comprising a hydrophobic moiety, and (C) a third repeating unit C, and wherein:
the weight average molecular weight of the terpolymer is less than 10,000 Da; and
the terpolymer is selected from the group consisting of:

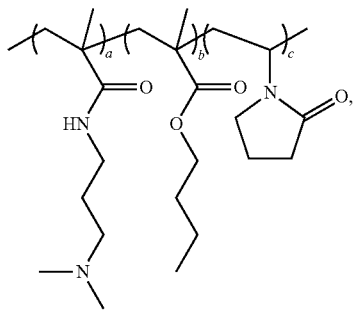

-continued

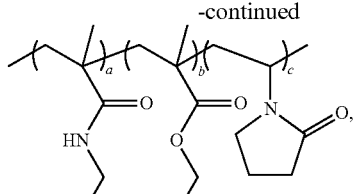

and combinations thereof.

10. The composition according to claim 9, wherein the terpolymer exhibits antimicrobial activity against a microbe selected from the group consisting of *S. aureus, E. coli, P. aeruginosa, A. niger, C. albicans*, and mixtures thereof.

11. The terpolymer according to claim 1 wherein the terpolymer is a random, block, or alternating polymer.

12. The terpolymer according to claim 1 wherein the terpolymer is:

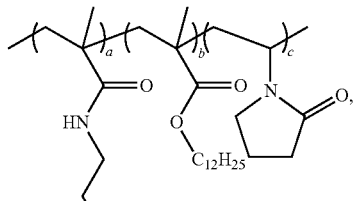

13. The terpolymer according to claim 1 wherein the terpolymer is:

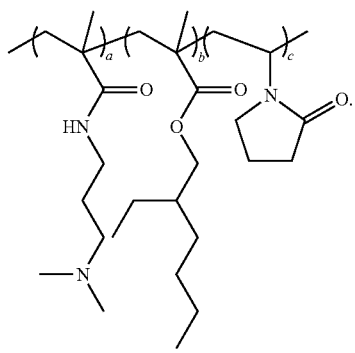

14. The terpolymer according to claim 1 wherein the terpolymer is:

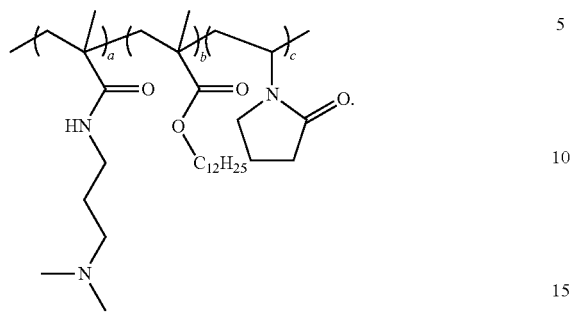

15. The terpolymer according to claim 1 wherein a ranges from 12% to 64%, b ranges from 20% to 40%, and c ranges from 12% to 64% (all molar ratios).

16. The terpolymer according to claim 14 wherein a ranges from 12% to 64%, b ranges from 20% to 40%, and c ranges from 12% to 64% (all molar ratios).

17. The terpolymer according to claim 12 wherein a ranges from 12% to 64%, b ranges from 20% to 40%, and c ranges from 12% to 64% (all molar ratios).

18. The terpolymer according to claim 13 wherein a ranges from 30% to 40%, b ranges from 20% to 40%, and c ranges from 30% to 40% (all molar ratios).

* * * * *